US006326152B1

(12) United States Patent
Holzmayer et al.

(10) Patent No.: US 6,326,152 B1
(45) Date of Patent: Dec. 4, 2001

(54) COMPOSITIONS AND METHODS FOR INHIBITING HUMAN IMMUNODEFICIENCY VIRUS INFECTION BY DOWN-REGULATING HUMAN CELLULAR GENES

(75) Inventors: Tanya A. Holzmayer; Stephen J. Dunn; Andrew Dayn, all of Mountain View, CA (US)

(73) Assignee: Subsidiary No. 3, Inc., Wilmington, NC (US)

( * ) Notice: Subject to any disclaimer, the term of this patent is extended or adjusted under 35 U.S.C. 154(b) by 0 days.

(21) Appl. No.: 09/587,674

(22) Filed: Jun. 5, 2000

Related U.S. Application Data

(62) Division of application No. 08/867,314, filed on Jun. 2, 1997, now Pat. No. 6,071,743.

(51) Int. Cl.[7] .............................. C12Q 1/68; C12Q 1/32; G01N 33/53; C12N 9/88; C12N 5/02
(52) U.S. Cl. .............................. 435/6; 435/7.1; 435/7.71; 435/26; 435/236; 435/325
(58) Field of Search .............................. 435/6, 7.1, 7.71, 435/26, 320.1, 325, 236

(56) References Cited

U.S. PATENT DOCUMENTS 5,256,534    10/1993   Butera et al. ..................... 435/5

FOREIGN PATENT DOCUMENTS

| 594881     | 10/1992 | (EP) . |
| WO 9007936 | 7/1990  | (WO) . |
| WO 9012087 | 10/1990 | (WO) . |
| WO 9207071 | 4/1992  | (WO) . |
| WO 9306216 | 4/1993  | (WO) . |
| WO 93 11230| 6/1993  | (WO) . |
| WO 94 10302| 5/1994  | (WO) . |
| WO 9416060 | 7/1994  | (WO) . |
| WO 94 26877| 11/1994 | (WO) . |
| WO 95 13379| 5/1995  | (WO) . |

OTHER PUBLICATIONS

Pettit et al., 1993, Persp. Drug. Discov. Design 1:69–83.
Condra et al., 1995, Nature 374:569–571.
Torres et al., 1997, Infec. Med. 14:142–160.
Sullenger et al., 1990, Cell 63:601–608.
Sullenger et al., 1991, J. Virol 65:6811–6816.
Lisziewicz et al., 1993, New Biol. 3:82–89.
Sarver et al., 1990, Science 247:1222–1225.
Wescrasinghi et al., 1991, J. Virol. 65:5531–5534.
Dropulic et al., 1992, J. Virol.66:1432–1441.
Yu et al., 1993, Proc. Natl. Acad. Sci. USA 90:6340–6344.
Yu et al., 1995, Proc. Natl. Acad. Sci. USA 92:699–703.
Sezakiel et al., 1991, J. Virol. 65:468–472.
Rhodes et al., 1991, AIDS 5:145–151.
Sezakiel et al., 1992, J. Virol 66:5576–5581.
Joshi et al., 1991, J. Virol5524–5530.
Pearson et al., 1990, Proc. Natl. Acad. Sci., USA 87:5079–5083.
Modesti et al., 1991, New Biol. 3:759–768.
Trono et al., 1989, Cell 59:113–120.
Bushschacher et al., 1995, J. Virol. 69:1344–1348.
Junker et al., 1996, J. Virol. 70:7765–7772.
Woffendin et al., 1996, Proc. Natl. Acad. Sci., USA 93:2889–2894.
Moore, 1997, Science 276:51–52.
Cohen, 1997, Science 275:1261.
Gudkov & Roninson, 1996, Methods in Molecular Biology 69:229–231.
Bednarik & Folks, 1992, AIDS 6:3–16.
Poli & Fauci, 1992, AIDS Res. Human Retoviruses 9:191–197.
Foley et al., 1965, Cancer 18:522–529.
Kozak et al., 1994, Biochemie 76:815–821.
Anderson et al., 1981, Nature 290–457.
Chomym et al., 1985, Nature 314:592.
Chomym et al., 1986, Science 234:619.
Walker et al., 1992, J. Mol. Biol. 226:1051.
Fearnley et al., 1989, EMBO J. 8:665.
Pilkington et al., 1989, Biochem. 28:3257.
Koike et al., 1992, Proc. Natl. Acad. Sci. USA 89:1963–1967.
Koike et al., 1993, Genel59:261–266.
Kato et al., 1989, Proc. Natl. Acad. Sci. USA 86:7861–7865.
Ou et al., 1995, J. Biol. Chem. 270:18051.
Li et al., 1996, Proc. Natl. Acad. Sci. USA 93:9606.
David et al., 1993, J. Biol. Chem. 268:9585–9592.
Tsai et al, 1991, Biol. J. Chem. 266:23053–23059.
Hochtrasser, 1995, Curr. Opin. Cell. Biol. 7:773–785.

(List continued on next page.)

Primary Examiner—Andrew Wang
(74) Attorney, Agent, or Firm—McDonnell Boehnen Hulbert & Berghoff

(57) ABSTRACT

The present invention relates to the identification of several human genes as cellular targets for the design of therapeutic agents for suppressing human immunodeficiency virus (HIV) infection. These genes encode intracellular products which appear to be necessary for HIV replication, as evidenced by an inhibition of HIV infection in cells in which the expression of these genes is down-regulated. Therefore, inhibitors of these genes and their encoded products may be used as therapeutic agents for the treatment and/or prevention of HIV infection. In addition, the invention also relates to methods for identifying additional cellular genes as therapeutic targets for suppressing HIV infection, and methods of using such cellular genes and their encoded products in screening assays for selecting additional inhibitors of HIV.

15 Claims, 16 Drawing Sheets

OTHER PUBLICATIONS

Scherer et al., 1995, Proc. Natl. Acad. Sci. USA 92:11259–11263.
Everett et al., 1997, EMBO J. 16:556–577.
Huang et al., 1995, Science 270:1828–1831.
Zhu et al., 1996, Proc. Natl. Acad. Sci. USA 93:3275–3279.
Shimuzu et al., 1989, J. Immunol. 143:2457–2463.
Huet et al., 1989, J. Immunol. 143:798–801.
Stamenkovich et al., 1989, Cell 56:1057–1062.
Bartolazzi et al, 1996, J. Cell Biol. 132:1199–1208.
Guo & Hildreth, 1993, J. Immunol. 151:2225–2236.
Walton and Dixon, 1993, Ann. Rev. Biochem. 62:101–120.
Zolnierowiez & Hemmings, 1994, Trends Cell Biol. 4:61–64.
Nandi and Banerjee, 1995, Med. Hypothesis 45:476–480.
Ensoli et al., 1990, Nature 345:84–86.
Balliet et al., 1994, Virology 200:623–631.
Venkatesh et al., 1990, Virology 176:39–47.
Camaur et al., 1997, Virology 71:6834–6841.
Kim et al., 1996, Oncogene 13:2275–2279.
Keyse and Emslie, 1992, Nature 359:644–647.
Liscovitch and Cantley, 1994, Cell 77:329–334.
Volinina et al., 1995, EMBO J. 14:3339–3348.
Graziani et al., 1996, J. Biol. Chem. 271:6590–6593.
Garcia, 1997, C.R. Acad. Sci.III 320:505–508.
Mazerolles et al., 1997, Eur.J. Immunol.27:2457–2465.
Borgatti et al., 1997, Eur. J. Immunol. 27:2805–2811.
Duttaroy et al., 1998, Exp. Cell Res. 238:168–176.
Uetsuki et al, 1989 J. Biol. Chem. 264:5791–5798.
Mehot et al., 1996, RNA 2:38–50.
Abramson et al., 1987, J. Biol. Chem. 262:3826–3832.
Ray et al., 1985, J. Biol. Chem. 260:7651–7658.
Rozen et al, 1990, Mol. Cell. Biol. 10:1134–1144.
Altmann et al., 1995, EMBO J. 14:3820–3827.
Methot et al., 1996, Mol. Cell. Biol. 16:5328–5334.
Milburn et al., 1990, EMBO J. 9:2783–2790.
Wozney et al., 1988, Science 242:1528–1534.
Rodier et al., 1999, Exp. Cell. Res. 249:337–348.
Rouault et al., 1992, EMBO J. 11:1663–1670.
Pulford et al., 1999, Immunology 96:262–271.
Zu et al., 1996, Blood 87:5287–5296.
Carballo et al., 1996, J. Immunol. 156:1709–1713.
Han et al., 1992, J. Virol. 66:4065–4072.
Mateer et al., 1998, J. Biol. Chem. 273:35339–35346.
Tung et al., 1997 FEBS Lett. 401: 197–201.
Summers et al., 1993, Gene 136:185–192.
Frolova et al., 1994, Nature 372:701–703.
Andjelkovic et al., 1996, EMBO J. 15:7156–67.
Zhu, 1997, Arch. Biochem. Biophys. 339:210–217.
Zigman et al., 1993, Endocrinology 133:2508–2514.
Truant et al., 1999, Mol. Cell Biol, 19:1210–7.
Jenkins et al., 1998, J. Cell Biol, 143:875–885.
Vodicka et al., 1998, Genes Dev, 12:175–185.
Hlavin et al., 1991, Genomics 11:416–423.
Horowitz et al., 1997, RNA 3:1374–1387.
Wang et al., 1997, J. Biol Chem. 272:17542–17550.
Flohr et al., 1992, Eur, J. Immunol. 22:975–979.
Zhu et al., 1989, J. Biol. Chem. 264:14556–14560.
Melhem et al., 1991, J. Biol. Chem. 266:17747–17753.
Mayer et al., 1998, Biochim. Biophys. Acta. 1395:301–308.
Fischer et al., 1996, J. Virol. 70:7153–7160.
Giallongo et al., 1990, Eur. J. Biochem, 190:567–573
Giallongo et al., 1986, Proc. Natl. Acad. Sci USA 83:6741–6745.
Russell et al., 1993, DNA Cell Biol. 12:157–175.
Handen et al., 1997, FEBS Lett. 410:301–302.
Cochi et al., 1995, Science, 270:1811–1815.
Gong et al., 1998, J. Biol Chem., 271:2599–2603.
Cho et al., 1997, Biomed. Pharmacother. 51:221–229.
Sanchez et al., 1997, Electrophoresis 18:150–155.
Walsh et al., 1995, J. Leukoc. Biol. 57:507–512.
Baudet et al., 1998, Cell Death Differ, 5:116–125.
MacDonald et al., 1999, Cytogenet Genet, 84:128–129.
Fukuski, 1999, FEBS Lett. 442:83.
Lambotte et al., 1996, DNA Cell Biol., 15:769–777.
Hu et al., 1996, Proc. Natl. Acad. Sci. USA 931060–1064.
Maki et al., 1990, Proc. Natl. Acad. Sci USA 87:5440–5443.
Meroni et al., 1997, EMBO J. 15–16:2892–906.
Chinen et al., 1995, Cytogenet Cell Genet. 70:215–217.
Schilling, 1998, Virology 247:74–85.
Raboudi, et al., 1992, J. Biol. Chem. 267:11930–11939.
Liu et al., 1996, J. Biol. Chem. 271:11817–11823.
Degli et al., 1994, Biochem. J. 301:161.
Friedrick et al., 1994, Eur. J. Biochem. 219:691.
Uchida et al., 1994, Int. J. Cancer 58:891.
Wyatt et al., 1995, Biochem. Pharmacol. 50:1599.
Shimomura et al., 1989, Arch. Biochem Biopys. 270:573.
Majamaa et al., 1985, Biochem. J. 229:127–133.
Yousefi et al., 1994, Proc. Natl. Acad. Sci. USA 91:10868–10872.
Lund–Johansen et al., 1996, Cytometry 25:182–190.
Coche et al, Nucleic Acids Res. 22:1322–1323.
Barre–Sinoussi et al., 1983 220:868–870.
Gallo et al., 1984, Science 224:500–503.
Teich et al., 1984 RNA Tumor Viruses, Weiss et al., eds., CSH–Press, pp. 949–956.
Varmus, 1988, Science 240:1427–1439.
Clavel et al., 1986, Science 233:343–346.
Guyader et al., 1987, Nature 326:662–669.
Dalgleish et al., 1984, Nature 312:763–767.
Klatzman et al., 1984, Nature 312:767–768.
Maddon et al., 1986, Cell 47:333–348.
Smith et al., 1986, Science 232:382–385.
Mitsuya et al., 1991, FASEB J. 5:2369–2381.
Mitsuya et al., 1990, Science 249:1533–1544.
Larder et al., 1989, Science 243:1731–1734.
Smith et al., 1987, Science 238:1704–1707.
Daar et al., 1990, Proc. Natl. Acad. Sci. USA 87:6574–6579.
Schooley et al., 1990, Ann. Int. Med. 112:247–253.
Kahn et al., 1990, Ann. Int. Med. 112–254–261.
Yarchoan et al., 1989, Proc. Vth Int. Conf. on AIDS, p. 564, MCP 137.
Erickson, 1990, Science 249:527–533.
Ventakash et al., 1990, Proc. Natl. Acad. Sci. USA 87:8746–8750.
Brady et al., 1994, Proc. Natl. Acad. Sci. USA 91:365–369.
Malim et al., 1992, J. Exp. Med. 176:1197.
Bevec et al., 1992, Proc. Natl. Acad. Sci. USA 89:9870–74.
Woffendin et al., 1994, Proc. Natl. Acad. Sci. USA 91:11581–85.
Lee et al., 1994, J. Virology 68:8254–64.
Marasco et al., 1993, Proc. Natl. Acad. Sci. USA 90:7889–93.
Chatterjee et al., 1992, Science 258:1485.
Ojwang et al., 1992 Proc. Natl. Acad. Sci. USA 89:10802–06.
Yamada et al., 1994, Gene Therapy 1:38–45.
Miller and Rosman, 1989, BioTechniques 7:980.

Miller and Buttimore, 1986, Mol. Cell. Biol. 6:2895–2902;ATCC CRL #9078.
Bednarkik and Folks, 1992, AIDS 6:3–16.
Poli and Fauci, 1992, AIDS Res. Human Retoviruses 9:191–197.

Foley et al., 1965, Cancer 18:522–29.
Nara & Fischinger, 1988, Nature 322:469–70.
Bittner et al., 1987, Methods in Enzymol. 153:516–544.
Logan & Shenk, 1984, Proc. Natl. Acad. Sci. USA 81:3655–3659.

```
AGATCCTATT GGTGCGTGGG CTTTGTATGA TTATGGGCGT
AGATTAGTAG TAGTTACTGG TTGAACATTG TTTGTTGGTG
TATATATTGT AATTGGGATT GCTCGGGGA ATAGGTTATG
TGATTAGGAG TAGGG
```

GATCCTCCCG AATCAACCCT GACCCTCTC CTTCATAAAT
TATTCAGCTT CCTACACTAT TAAAGTTTAC CACAACCACC
ACGCCATCAT ACTCCTTCAC

CATCAGCCCT TCTTAACATC TACTTCTACC TACGCCTAAT
CTACTCCACC TCAATCACAC TACTCCCCAT ATCTAACAAC
GTAAAAATAA AATGACAGTT TGAGCATACA AAACCCACCC
CATTCCTCCC CACACTCATC GCC

```
GTGAAAGAGT ATGATGGGGT GGTGGTTGTC GTAAACTTTA
ATAGTGTAGG AAGCTGAATA ATTTATAAAG GAGAGGGGAC
AGGGTTGATT CGGGAGGATC
```

```
GAAGAAGCAG GCCGGATGTC AGAGGGGTGC CTTGGGTAAC
CTCTGGGACT CAGAAGTGAA AGGGGGCTAT TCCTAGTTTT
ATTGCTATAG CCATTATGAT TATTAATGAT GAGTAT
```

TCCTAGTCCT CACAATCATG GCAAGCCAGC GCCACTTATC
CAGTGAACCA CTATCACGAA AAAAACTCTA CCTCTCTATA
CTAATCTCCC TACAAATCTC CTTAATTATA ATATTCACAA
CCACAGA

```
GCGCAAAGCA CGCGACATGG TGGGGCAGGT GGCCATCACA
AGGATTGAGC AGCTGTCGCC ATTCCCCTTT GACCTCCTGC
TGAAGGAGGT GCAGAAGTAC CCCAA
```

GAAATCCTGG AGGCCAGTGA TGGGATCATG GTGGCTCGCG
GTGATCTAGG CATTGAGATT CCTGCAGAGA AGGTCTTCCT
TGCTCAGAAG ATGATAATTG GACGG

GGTTGTCAAT CACAGGTCGC CACCAGACAC CACATCCAGG
AGCTGACTCA CATCTAGGGT TGGCAATCTG AGGAGCCTCC
CATTCTCCAT CCATGTCTTC ATCCCAA

CCACATTGAA CCCAATGGTA GGGATGGTGG TGACGATCTC
CCCCAGTTTC AGCTTGTATA GGATGGTGGT CTTTCCTGCG
GCATCCAGGC CCACCATCAG GATGCGCATC TCCTTCTTCC
C

COMPOSITIONS AND METHODS FOR INHIBITING HUMAN IMMUNODEFICIENCY VIRUS INFECTION BY DOWN-REGULATING HUMAN CELLULAR GENES

This application is a divisional of U.S. Ser. No. 08/867,314, filed Jun. 2, 1997, now U.S. Pat. No. 6,071,743, issued Jun. 6, 2000, the disclosure of which is incorporated by reference in its entirety herein.

INTRODUCTION

The present invention relates to the identification of several human genes as cellular targets for the design of therapeutic agents for suppressing human immunodeficiency virus (HIV) infection. These genes encode intracellular products which appear to be necessary for HIV replication, as evidenced by an inhibition of HIV infection in cells in which the expression of these genes is down-regulated. Therefore, inhibitors of these genes and their encoded products may be used as therapeutic agents for the treatment and/or prevention of HIV infection. In addition, the invention also relates to methods for identifying additional cellular genes as therapeutic targets for suppressing HIV infection, and methods of using such cellular genes and their encoded products in screening assays for selecting additional inhibitors of HIV.

BACKGROUND OF THE INVENTION
The Human Immunodeficiency Virus

The primary cause of acquired immunodeficiency syndrome (AIDS) has been shown to be HIV (Barre-Sinoussi et al., 1983, Science 220:868–870; Gallo et al., 1984, Science 224:500–503). HIV causes immunodeficiency in an individual by infecting important cell types of the immune system, which results in their depletion. This, in turn, leads to opportunistic infections, neoplastic growth and death.

HIV is a member of the lentivirus family of retroviruses (Teich et al., 1984, RNA Tumor Viruses, Weiss et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, 1988, Science 240:1427–1439). There are at least two distinct subtypes of HIV: HIV-1 (Barre-Sinoussi et al., 1983, Science 220:868–870; Gallo et al., 1984, Science 224:500–503) and HIV-2 (Clavel et al., 1986, Science 233:343–346; Guyader et al., 1987, Nature 326:662–669). Genetic heterogeneity exists within each of these HIV subtypes.

$CD4^+$ T cells are the major targets of HIV infection because the CD4 cell surface protein acts as a cellular receptor for HIV attachment (Dalgleish et al., 1984, Nature 312:763–767; Klatzmann et al., 1984, Nature 312:767–768; Maddon et al., 1986, Cell 47:333–348). Viral entry into cells is dependent upon viral protein gp120 binding to the cellular CD4 receptor molecule (McDougal et al., 1986, Science 231:382–385; Maddon et al., 1986, Cell 47:333–348).
HIV Treatment HIV infection is pandemic and HIV-associated diseases have become a world-wide health problem. Despite considerable efforts in the design of anti-HIV modalities, there is, thus far, no successful prophylactic or therapeutic regimen against AIDS. However, several stages of the HIV life cycle have been considered as potential targets for therapeutic intervention (Mitsuya et al., 1991, FASEB J. 5:2369–2381). For example, virally-encoded reverse transcriptase has been a major focus of drug development. A number of reverse-transcriptase-targeted drugs, including 2',3'-dideoxynucleotide analogs such as AZT, ddI, ddC, and ddT have been shown to be active against HIV (Mitsuya et al., 1990, Science 249:1533–1544). While beneficial, these nucleotide analogs are not curative, probably due to the rapid appearance of drug resistant HIV mutants (Lander et al., 1989, Science 243:1731–1734). In addition, these drugs often exhibit toxic side effects, such as bone marrow suppression, vomiting, and liver abnormalities.

Another stage of the HIV life cycle that has been targeted is viral entry into the cells, the earliest stage of HIV infection. This approach has primarily utilized recombinant soluble CD4 protein to inhibit infection of $CD4^+$ T cells by some HIV-1 strains (Smith et al., 1987, Science 238:1704–1707). Certain primary HIV-1 isolates, however, are relatively less sensitive to inhibition by recombinant CD4 (Daar et al., 1990, Proc. Natl. Acad. Sci. USA 87:6574–6579). To date, clinical trials of recombinant, soluble CD4 have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

Additionally, the later stages of HIV replication which involve crucial virus-specific secondary processing of certain viral proteins and enzymes have been targeted for anti-HIV drug development. Late stage processing is dependent on the activity of a virally-encoded protease, and drugs including saquinavir, ritonavir, and indinavir have been developed to inhibit this protease (Pettit et al., 1993, Persp. Drug. Discov. Design 1:69–83). With this class of drugs, the emergence of drug resistant HIV mutants is also a problem; resistance to one inhibitor often confers cross resistance to other protease inhibitors (Condra et al., 1995, Nature 374:569–571). These drugs often exhibit toxic side effects such as nausea, altered taste, circumoral parethesias and nephrolithiasis.

Antiviral therapy of HIV using different combinations of nucleoside analogs and protease inhibitors have recently been shown to be more effective than the use of a single drug alone (Torres et al., 1997, Infec. Med. 14:142–160). However, despite the ability to achieve significant decreases in viral burden, there is no evidence to date that combinations of available drugs will afford a curative treatment for AIDS.

Other potential approaches for developing treatment for AIDS include the delivery of exogenous genes into infected cells. One such gene therapy approach involves the use of genetically-engineered viral vectors to introduce toxic gene products to kill HIV-infected cells. Another form of gene therapy is designed to protect virally-infected cells from cytolysis by specifically disrupting viral replication. Stable expression of RNA-based (decoys, antisense and ribozymes) or protein-based (transdominant mutants) HIV-1 antiviral agents can inhibit certain stages of the viral life cycle. A number of anti-HIV suppressors have been reported, such as decoy RNA of TAR or RRE (Sullenger et al., 1990, Cell 63:601–608; Sullenger et al., 1991, J. Virol. 65:6811–6816; Lisziewicz et al., 1993, New Biol. 3:82–89; Lee et al., 1994, J. Virol. 68:8254–8264), ribozymes (Sarver et al., 1990, Science 247:1222–1225; Wecrasinghe et al., 1991, J. Virol. 65:5531–5534; Dropulic et al., 1992, J. Virol. 66:1432–1441; Ojwang et al., 1992, Proc. Natl. Acad. Sci. U.S.A. 89:10802–10806; Yu et al., 1993, Proc. Natl. Acad. Sci. U.S.A. 90:6340–6344; Yu et al., 1995, Proc. Natl. Acad. Sci. U.S.A. 92:699–703; Yamada et al., 1994, Gene Therapy 1:38–45), antisense RNA complementary to the mRNA of gag, tat, rev, env (Sezakiel et al., 1991, J. Virol. 65:468–472;

Chatterjee et al., 1992, *Science* 258:1485–1488; Rhodes et al., 1990, *J. Gen. Virol.* 71:1965; Rhodes et al.,1991, *AIDS* 5:145–151; Sezakiel et al., 1992, *J. Virol.* 66:5576–5581; Joshi et al., 1991, *J. Virol.* 65:5524–5530) and transdominant mutants including Rev (Bevec et al., 1992, *Proc. Natl. Acad. Sci. U.S.A.* 89:9870–9874), Tat (Pearson et al., 1990, *Proc. Natl. Acad. Sci. U.S.A.* 87:5079–5083; Modesti et al., 1991, *New Biol.* 3:759–768), Gag (Trono et al., 1989, *Cell* 59:113–120), Env (Bushschacher et al., 1995, *J. Virol.* 69:1344–1348) and protease (Junker et al., 1996, *J. Virol.* 70:7765–7772).

Antisense polynucleotides have been designed to complex with and sequester the HIV-1 transcripts (Holmes et al., WO 93/11230; Lipps et al., WO 94/10302; Kretschmer et al., EP 594,881; and Chatterjee et al., 1992, *Science* 258:1485). Furthermore, an enzymatically active RNA, termed ribozyme, has been used to cleave viral transcripts. The use of a ribozyme to generate resistance to HIV-1 in a hematopoietic cell line has been reported (Ojwang et al., 1992, *Proc. Natl. Acad. Sci. USA* 89:10802–06; Yamada et al., 1994, *Gene Therapy* 1:38–45; Ho et al., WO 94/26877; and Cech and Sullenger, WO 95/13379). In preclinical studies, RevM10, a transdominant Rev protein, has been transfected ex vivo into CD4$^+$ cells of HIV-infected individuals and shown to confer survival advantage over cells transfected with vector only (Woffendin et al., 1996, *Proc. Natl. Acad. Sci. U.S.A.* 93:2889–2894).

Cellular Genes Necessary For HIV Replication

Evolution of an intracellular pathogen has resulted in the development of interactions of its genes and gene products with multiple cellular components. For instance, the interactions of a virus with a host cell involves binding of the virus to a specific cellular receptor(s), translocation through the cellular membrane, uncoating, replication of the viral genome, transcription of the viral genes, etc. Each of these events occurs in a cell and involves interactions with a cellular component. Thus, the life cycle of a virus can be completed only if the cell is permissive. Availability of amino acids and nucleotides for replication of the viral genome and protein synthesis, energy status of the cell, the presence of cellular transcription factors and enzymes all contribute to the propagation of the virus in the cell. Consequently, the cellular components, in part, determine host cell susceptibility to infection, and may be used as potential targets for the development of new therapeutic interventions. In the case of HIV, one cellular component which has been used towards this end is the cell surface molecule for HIV attachment, CD4.

Recently, it was reported that HIV entry into a susceptible cell requires the expression of a second receptor, the chemokine receptor (CCR5 or CXCR4), in addition to CD4 (Moore, 1997, *Science* 276:51–52). A chemokine receptor normally binds RANTES, MIP-1α and MIP-1β as its natural ligand. In the case of HIV infection, it has been proposed that CD4 first binds to gp120 of HIV on the cell surface followed by the binding of the complex to a chemokine receptor to result in viral entry into the cells (Cohen, 997, *Science* 275:1261). Therefore, chemokine receptors may present an additional cellular target for the design of HIV therapeutic agents. Inhibitors of HIV/chemokine receptor interactions are being tested as anti-HIV agents. However, there remains a need for the discovery of additional cellular targets for the design of anti-HIV therapeutics, particularly intracellular targets for disrupting viral replication after viral entry into a cell.

SUMMARY OF THE INVENTION

The present invention relates to compositions and methods for inhibiting HIV infection by down-regulating the expression and/or function of certain human cellular genes. In particular, it relates to several human cell-derived polynucleotides which inhibit HIV replication in susceptible cells. Each of the isolated polynucleotides corresponds to a portion of a cellular gene or a complement thereof, and is referred to herein as a genetic suppressor element (GSE). The cellular genes encode intracellular products which are necessary for a productive HIV infection. Additionally, small molecule inhibitors of the same cellular genes and their encoded products are also within the scope of the present invention. The invention also relates to methods for identifying additional cellular genes as therapeutic targets for suppressing HIV infection, and methods for using such cellular genes and their encoded products for selecting additional inhibitors of HIV.

The invention is based, in part, on the Applicants' discovery that polynucleotides isolated from human cells can prevent the activation of latent HIV-1 in a CD4$^+$ cell line as well as productive HIV infection, and that such polynucleotides correspond to fragments of certain human cellular genes. In that connection, any cellular or viral marker associated with HIV replication can be used to select for such polynucleotides or GSEs. An example of such a marker is CD4, which is conveniently monitored by using a specific antibody.

Based on substantial sequence identity (90–100%), several of the isolated GSEs correspond to portions of human cellular genes which encode different subunits of a mitochondrial enzyme complex, NADH dehydrogenase. In addition, inhibitors of this enzyme also inhibit HIV replication in susceptible host cells, including freshly isolated human CD4$^+$ T cells. Furthermore, additional GSEs have been selected which have substantial sequence identity (90–100%) with human cellular genes which encode 2-oxoglutarate dehydrogenase, M2-type pyruvate kinase, calnexin and ADP-ribosylation factor 3.

Among the GSEs selected to inhibit HIV replication, several function in the sense orientation, while others function in the antisense orientation. Not intending to be bound by any particular theory, the GSEs of the invention are believed to down-regulate a cellular gene by different mechanisms. The GSEs are expressed in a host cell by encoding RNA molecules that may or may not encode polypeptide products. GSEs in the sense orientation may exert their effects as transdominant mutants or RNA decoys. Transdominant mutants are expressed polypeptides which competitively inhibit the normal function of a wild-type protein in a dominant fashion. RNA decoys are protein binding sites that titrate out these proteins. GSEs in the antisense orientation may exert their effects as antisense RNA; i.e. polynucleotides complementary to the mRNA of the target gene. These polynucleotides bind to mRNA and block the translation of the mRNA. Some antisense polynucleotides may act directly at the DNA level to inhibit transcription. The down-regulation of a cellular gene by a GSE, in turn, removes a cellular component necessary for HIV replication, resulting in an inhibition of HIV infection.

A wide range of uses are encompassed by the invention including, but not limited to, HIV treatment and prevention by transferring GSEs as pharmaceutical compositions into HIV-susceptible cell types. For example, GSEs may be transferred into T cells, particularly CD4$^+$ T cells which are the major cell population targeted by HIV. Alternatively, GSEs may be transferred into hematopoietic stem cells in vitro followed by their engraftment in an autologous or histocompatible or even histoincompatible recipient. In another embodiment, any cells susceptible to HIV infection may be directly transduced or transfected with GSEs in vivo. In yet another embodiment, inhibitors of NADH dehydrogenase, 2-oxoglutarate dehydrogenase, M2-type pyruvate kinase, calnexin and ADP-ribosylation factor 3 may be used as pharmaceutical compositions in vivo to suppress HIV infection.

BRIEF DESCRIPTION OF THE DRAWINGS

FIG. 2. Nucleotide sequence (SEQ ID No: 1) of a GSE, CF-315, which is selected for its ability to maintain CD4 expression by OM10.1 cells after TNF-α induction. The nucleotide sequence disclosed in the figure is an antisense sequence of a molecule that has substantial sequence identity with a gene encoding the ND6 subunit of human NADH dehydrogenase.

FIG. 4. Nucleotide sequence (SEQ ID No: 2) of a GSE, CF-319, which is selected for its ability to maintain CD4 expression by OM10.1 cells after TNF-α induction. The nucleotide sequence disclosed in the figure has substantial sequence identity with a gene encoding the ND6 subunit of human NADH dehydrogenase.

FIG. 5. Nucleotide sequence (SEQ ID No: 3) of a GSE, CF-101, which is selected for its ability to maintain CD4 expression by OM10.1 cells after TNF-α induction. The nucleotide sequence disclosed in the figure has substantial sequence identity with a gene encoding the ND2 subunit of human NADH dehydrogenase.

FIG. 6. Nucleotide sequence (SEQ ID No: 4) of a GSE, CF-117, which is selected for its ability to maintain CD4 expression by OM10.1 cells after TNF-α induction. The nucleotide sequence disclosed in the figure is an antisense sequence of a molecule that has substantial sequence identity with a gene encoding the ND6 subunit of human NADH dehydrogenase.

FIG. 7. Nucleotide sequence (SEQ ID No: 5) of a GSE, CF-025, which is selected for its ability to prevent productive infection of CEM-ss cells by HIV. The nucleotide sequence disclosed in the figure is an antisense sequence of a molecule that has substantial sequence identity with a gene encoding the ND2 subunit of human NADH dehydrogenase.

FIG. 8. Nucleotide sequence (SEQ ID No: 6) of a GSE, CF-128, which is selected for its ability to prevent productive infection of CEM-ss cells by HIV. The nucleotide sequence disclosed in the figure has substantial sequence identity with a gene encoding the ND4 subunit of human NADH dehydrogenase.

FIG. 9. Nucleotide sequence (SEQ ID No:7) of a GSE, CF-004, which is selected for its ability to prevent productive infection of CEM-ss cells by HIV. The nucleotide sequence disclosed in the figure has substantial sequence identity with a gene encoding human 2-oxoglutarate dehydrogenase.

FIG. 10. Nucleotide sequence (SEQ ID No: 8) of a GSE, CF-113, which is selected for its ability to prevent productive infection of CEM-ss cells by HIV. The nucleotide sequence disclosed in the figure has substantial sequence identity with genes encoding human M2-type pyruvate kinase and cytosolic thyroid hormone binding protein.

FIG. 11. Nucleotide sequence (SEQ ID No: 9) of a GSE, CF-204, which is selected for its ability to prevent productive infection of CEM-ss cells by HIV. The nucleotide sequence disclosed in the figure is an antisense sequence of a molecule that has substantial sequence identity with a gene encoding human calnexin.

FIG. 12. Nucleotide sequence (SEQ ID No: 10) of a GSE, CF-001, which is selected for its ability to prevent productive infection of CEM-ss cells by HIV. The nucleotide sequence disclosed in the figure is an antisense sequence of a molecule that has substantial sequence identity with a gene encoding human ADP-ribosylation factor 3.

DETAILED DESCRIPTION OF THE INVENTION

Figure 1:
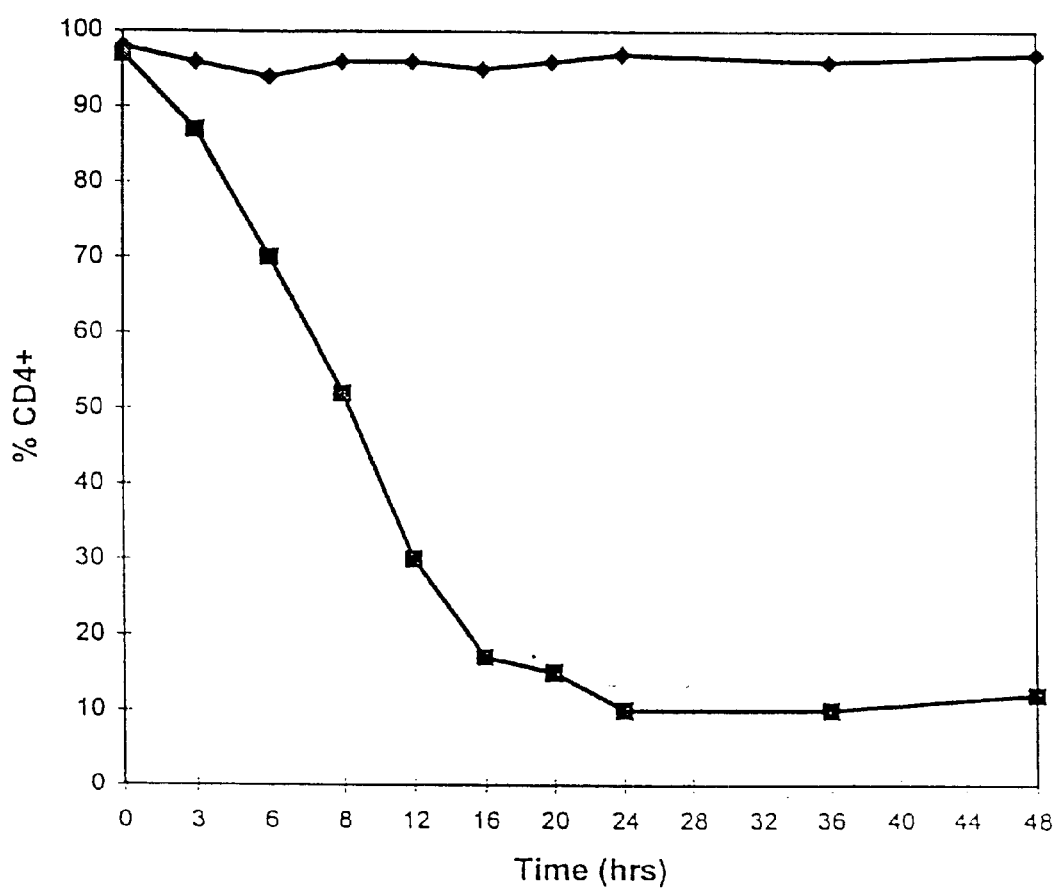
FIG. 1. Percentage of CD4+ OM10.1 cells diminishes after TNFα induction; TNF-induced cells, ■; uninduced cells, ♦.

Section 6, infra, illustrates two specific methods which have been used to select and isolate GSEs from a human cell-derived RFE library. These methods include the common steps of: 1) randomly fragmenting cell-derived cDNA into 100–700 base pair (bp) fragments; 2) inserting the fragments into expression vectors to form an expression library; 3) transferring the expression library into a population of cells containing an inducible latent HIV-1 provirus or susceptible to HIV infection; 4) selecting a subpopulation of cells which contain a subset of the expression library enriched for GSEs by monitoring the expression of a cellular or viral marker associated with HIV infection; and 5) recovering the GSEs from the selected cell population. The methods further include repetition of the aforementioned steps so that many rounds of successive selection can be performed. The selection of GSEs can be performed by monitoring the continued expression of a cellular marker such as CD4 or the decreased expression of a viral marker such as p24 or gp120 using an antibody.

The invention is discussed in more detail in the subsections below, solely for purposes of description and not by way of limitation. For clarity of discussion, the specific procedures and methods described herein are exemplified using OM10.1 cells, CEM-ss cells, tumor necrosis factor-alpha (TNF-α), an anti-CD4 antibody, and an anti-p24 antibody, but they are merely illustrative for the practice of the invention. Analogous procedures and techniques are equally applicable to isolating GSEs from other cellular DNA, utilizing any cell line and any marker associated with HIV infection that can be easily assayed.

Preparation and Transfection of a Mammalian Cell-derived RFE Library

A cell-derived RFE library can be constructed from nucleic acid molecules of any mammalian cells, preferably from cDNA of HIV-susceptible cells. In that regard, Section 6, infra, demonstrates that GSEs can be selected from HL-60 cells that are naturally susceptible to HIV infection and from HeLa cells which are not naturally susceptible to HIV infection due to the lack of CD4 expression. However, it has been shown that expression of CD4 on the surface of HeLa cells by means of a retroviral vector renders the cells susceptible to HIV infection. Therefore, cell types not normally susceptible to HIV infection may still be useful as a source of genetic material for the construction of RFE libraries. It is also preferred that a normalized cDNA library is prepared (Gudkov and Roninson, 1996, *Methods in Molecular Biology* 69:229–231). DNA is first treated with enzymes to produce randomly cleaved fragments. This can be conveniently performed by DNase I cleavage in the presence of $Mn^{++}$ (Roninson et al., U.S. Pat. No. 5,217,889, column 5, lines 5–20). Thereafter, the randomly cleaved DNA are size fractionated by gel electrophoresis. Fragments of between 100 and 700 bp are the preferred lengths for constructing RFE libraries. Single strand breaks of the size-selected fragments are repaired by methods well known in the art.

The fragments are ligated with 5' and 3' adaptors, which are selected to have non-cohesive restriction sites so that each fragment can be inserted into an expression vector in an oriented fashion. Further, the 5' adaptor contains a start (ATG) codon to allow the translation of the fragments which contain an open reading frame in the correct phase. The fragments are then inserted into appropriate expression vectors. Any expression vector that results in efficient expression of the fragments in host cells can be used. In a preferred embodiment viral-based vectors such as the retroviral vectors LNCX (Miller and Rosman, 1989, BioTechniques 7:980) and LNGFRM are exemplified. Alternatively, adenovirus, adeno-associated virus and Herpes virus vectors may also be used for this purpose.

When viral-based vectors are used, the ligated vectors are first transfected into a packaging cell line to produce viral particles. For retroviral vectors, any amphotropic packaging line such as PA317 (Miller and Buttimore, 1986, *Mol. Cell. Biol.* 6:2895–2902; ATCC CRL #9078) may be used to efficiently produce virus. In a preferred embodiment of the invention, the viral vector also contains a selectable gene, such as the $neo^r$ gene or a truncated nerve growth factor receptor (NGFR) gene, which allows isolation of the cells that contain the vector.

The number of independent clones present in each RFE expression library may vary. In a preferred embodiment, libraries of cell-derived cDNA of about $10^6$ to $10^8$ independent clones may be used.

Selection of GSEs in HIV-injected Cells

In a specific embodiment illustrated by way of example in Section 6, infra, OM10.1 cells are used to select for GSEs, and they are maintained in conventional tissue culture as described in Butera (U.S. Pat. No. 5,256,534). The purpose of using OM10.1 cells for the selection of GSEs is that they contain a latent HIV-1 provirus which is inducible by TNF-α. Other cell lines may be similarly engineered with an inducible HIV provirus. Examples of cell lines that are infected with latent HIV include, but are not limited to, U1, U33, 8E5, ACH-2, LL58, THP/HIV and UHC4 (Bednarik and Folks, 1992, AIDS 6:3–16). A variety of agents have been shown to be capable of inducing latent HIV-infected cells, and these include TNF-α, TNF-β, interleukins-1, -2, -3, -4 and -6, granulocyte-macrophage colony stimulating factors, macrophage-colony stimulating factors, interferon-γ, transforming growth factor-β, PMA, retinoic acid and vitamin D3 (Poli and Fauci, 1992, AIDS Res. Human Retroviruses 9:191–197). Alternatively, GSEs may be selected on the basis of their ability to directly protect HIV susceptible cells from HIV infection (see Section 5.5, infra).

The HIV-infected cells may be transferred with the cell-derived RFE library by any technique well known in the art that is appropriate to the vector system employed. In one embodiment of the invention, the viral vector also contains a selectable marker in addition to a random fragment of cellular DNA. A suitable marker is the $neo^r$ gene, which permits selection by the drug G-418. In a preferred embodiment, the viral vector contains a truncated low affinity nerve growth factor receptor (NGFR) which permits selection of the cells using an anti-NGFR monoclonal antibody. In alternative embodiments, the multiplicity of infection of the virions of the library is adjusted so that pre-selection for cells that are transduced by the vector is not needed.

In the case of OM10.1 cells, the transduced cell population is treated with 10 U/ml TNF-α for a period of 24–72 hours and preferably about 24 hours according to the method of Butera. The activation of the latent HIV-1 provirus in OM10.1 can be detected by the suppression of the cell surface CD4. It is believed that viral protein gp120 binds to CD4 in the cytoplasm, which prevents subsequent expression of CD4 on the cell surface. Clones that are resistant to HIV replication continue to express cell surface CD4. Such clones can be selected by cell sorting using any antibody staining technique for CD4 and a fluorescence activated cell sorter (FACS).

The fraction of $CD4^+$ cells that have been transduced with the RFE library can be compared with cells transduced with an expression library consisting of the vector only. An increased relative difference between the cell-derived RFE library and the control library can be found with each additional round of TNF-A induction. Thus, in the preferred embodiment of the invention there are at least two cycles of induction, selection and recloning before the GSEs are recovered from the cells for further characterization.

Recovery of GSEs from the Selected-Cells

After selection, specific polynucleotides corresponding to the GSEs can be recovered from cells that continue to express CD4 following induction of the latent HIV provirus by TNF-α. The specific GSEs are recovered from genomic DNA isolated from $CD4^+$ cells sorted by FACS after TNF-α induction. The GSEs in this population are recovered by PCR amplification using primers designed from the sequences of the vector.

The recovered GSEs can be introduced into an expression vector as discussed in Section 5.1, supra. The resultant GSEs expression library is known as a secondary library. The secondary library may utilize the same or a different vector from that used for the construction of the primary library. The secondary library may be transduced into another cell population and the resultant population selected, recloned and processed as described herein.

Additionally, each individually recovered GSE can be inserted into cloning vectors for determining its specific nucleotide sequence and its orientation. The sequence of the GSE is then compared with sequences of known genes to determine the portion of the cellular gene with which it corresponds. Alternatively, the PCR products may be directly sequenced to determine their nucleotide sequences.

Concurrently, the isolated GSEs can be analyzed to determine their minimal core sequences. A core sequence is a common sequence found by comparison of GSEs with overlapping sequences. The GSEs are further tested for their ability to protect previously uninfected cells from HIV infection.

In addition to the specific nucleotide sequences depicted in FIG. 2 (SEQ ID NO:1) and FIGS. 4–12 (SEQ ID NOS:2–10), nucleotide sequences capable of hybridizing to these sequences or their complements under highly or moderately stringent hybridization conditions are within the scope of the invention. Also included are GSEs with conservative nucleotide substitutions which produce the same polypeptide products. Highly stringent hybridization conditions may be defined as hybridization to-filter-bound DNA in 0.5 M $NaHPO_4$, 7% sodium dodecyl sulfate (SDS), 1 mM EDTA at 65° C., followed by washing in 0.1×SSC/0.1% SDS at 68° C. (Ausubel F. M. et al., eds, 1989, Current Protocols in Molecular Biology, Vol. I, Green Publishing Associates, Inc., and John Wiley & Sons, Inc., New York at p. 2.10.3). Moderately stringent conditions may be defined as hybridizations carried out as described above, followed by washing in 0.2×SSC/0.1% SDS at 42° C. (Ausubel et al., 1989, supra).

Determination of Core Sequences of Cell-derived GSEs

The present invention also includes methods for determining the core sequence of each GSE. This may be done by comparing overlapping sequences of independently derived GSEs. Alternatively, GSEs may be altered by additions, substitutions or deletions and assayed for retention of HIV-suppressive function. Alterations in the GSEs sequences may be generated using a variety of chemical and enzymatic methods which are well known to those skilled in the art. For example, oligonucleotide-directed mutagenesis may be employed to alter the GSE sequence in a defined way and/or to introduce restriction sites in specific regions within the sequence. Additionally, deletion mutants may be generated using DNA nucleases such as Bal 31 or Exo III and S1 nuclease. Progressively larger deletions in the GSE sequences may be generated by incubating the DNA with nucleases for increased periods of time (See Ausubel, et al., 1989 Current Protocols for Molecular Biology, for a review of mutagenesis techniques).

The altered sequences may be evaluated for their ability to suppress expression of HIV proteins such as p24 in appropriate host cells. It is within the scope of the present invention that any altered or shortened GSE polynucleotides that retain their ability to suppress HIV infection may be incorporated into recombinant expression vectors for further use.

Protection of Uninfected Cells by GSEs Against HIV Infection

In order to confirm that the selected GSEs can protect uninfected cells from HIV infection, the GSEs may be transferred into HIV susceptible host cells, followed by HIV infection. In this connection, GSEs also may be directly selected from a RFE library for their ability to prevent productive infection by HIV, as shown in a specific embodiment exemplified in Section 6, infra. Protection experiments can be performed in any cell type that takes up the potential GSEs and which is otherwise susceptible to HIV infection. In a preferred embodiment by way of example, the CEM-ss cell line is used (Foley et al., 1965, Cancer 18:522–29). The use of CEM-ss cells as targets for quantitative infectivity of HIV-1 has been described by Nara & Fischinger (1988, Nature 322:469–70). Other cell lines that are susceptible to HIV infection include, but are not limited to, HUT-78, H9, Jurkat E6-1, A3.01, U-937, AA-2, HeLa $CD4^+$ and C8166.

The test of the potential GSEs can be performed using the same expression vector system as that employed in the RFE library transduction of cells during initial selection steps. In other embodiments, the vector system can be modified to achieve higher levels of expression, e.g., the linkers can be employed to introduce a leader sequence that increases the translational efficiency of the message. One such sequence is disclosed by Kozak, 1994, Biochemie 76:815–821.

Another way of testing the effectiveness of a potential GSE against HIV is to determine how rapidly HIV-1 variants develop that can negate the effects of that element: Such a test includes infection of a culture of susceptible cells such as CEM-ss cells at a low multiplicity of infection and repeatedly assaying the culture to determine whether and how quickly HIV-1 infection becomes widespread. The range of useful multiplicities of infection is between about 100 to 1000 tissue culture infectious units ($TCID_{50}$) per-$10^6$ CEM-ss cells. The $TCID_{50}$ is determined by an endpoint method and is important for determining the input multiplicity of infection (moi).

A parameter that correlates with the development in the test culture of HIV-1 strains that are resistant to the effects of the potential GSEs is the fraction of cells that are infected in the culture. This fraction can be determined by immunofluorescent staining with an antibody specific for the HIV-1 p24 antigen of fixed permeabilized cells. Commercially available reagents are suitable for performing such tests (Lee et al., 1994, J. Virol. 68:8254–8264).

In Section 6.2, infra, several GSEs were tested for their ability to protect CEM-ss cells from infection with HIV-1 strain SF2. Uninfected cells were transduced with a retroviral construct containing either vector DNA or a GSE polynucleotide. Non-transduced cells were eliminated by selection of $NGFR^+$ cells by an antibody or by exposure to the selection agent, G-418. The percentage of $p24^+$ cells was determined at specific time points post infection. The results demonstrate that the GSEs tested are able to protect against productive HIV-1 infection in susceptible host cells.

The nucleotide sequences of the selected GSEs with HIV-inhibitory activities may be compared with known nucleotide sequences in the GenBank. The GSEs described in Section 6, infra, have substantial sequence identity, i.e., 90%–100%, with cDNAs of known cellular genes. Thus, these GSEs correspond to fragments of the cellular genes. Experiments are performed to further determine whether agents that down-regulate such genes and inhibitors that antagonize the activities of their gene products could also be used to inhibit HIV infection. In Section 7.2, infra, inhibitors of NADH dehydrogenase are shown to directly inhibit HIV infection in human cells. This finding demonstrates that host cell-derived polynucleotides possess anti-HIV activities, and in addition, their sequence identity with certain cellular genes may be used to identify cellular genes and gene products as targets for the development-of additional HIV therapeutics.

Uses of GSEs

Another aspect of the present invention is the use of the isolated GSEs against HIV infection prophylactically and therapeutically. A functionally active fragment of a GSE and a GSE containing conservative nucleotide substitutions as functional equivalents of a GSE are also within the scope of the present invention. In that connection, GSEs or functional equivalents thereof operably linked to a regulatory sequence that controls their expression may be transferred into any HIV-susceptible host cells such as $CD4^+$ T cells or hematopoietic progenitor cells such as $CD34^+$ cells obtained from bone marrow or mobilized peripheral blood, by any DNA transfer techniques well known in the art such as electroporation, transfection or transduction, followed by transplantation of the cells into a recipient. When the GSE-containing progenitor cells differentiate in vivo, the progeny cells express the GSEs and become resistant to HIV.

Alternatively, GSEs may be directly administered in vivo using a gene therapy expression vector. In particular, GSEs can be delivered or transferred into CD4$^+$ T cells in both HIV-infected or uninfected individuals to protect against development of HIV infection. GSEs can also be transferred into stromal cells, including macrophages.

Expression vectors derived from viruses such as retroviruses, adenovirus, adeno-associated virus, herpes viruses, or papilloma viruses may be used for delivery of recombinant GSEs into the targeted cell population. Methods which are well known to those skilled in the art can be used to construct recombinant viral vectors containing a GSE polynucleotide operably linked to a promoter that facilitates its expression (Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). In a specific embodiment by way of example, the GSE polynucleotides were inserted into a retroviral vector. In cases where an adenovirus is used as an expression vector, a GSE may be ligated to an adenovirus transcription-translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing GSEs in infected hosts (Logan & Shenk, 1984, *Proc. Natl. Acad. Sci. USA* 81:3655–3659).

Alternatively, a recombinant GSE polynucleotide can be delivered into a target cell by a non-viral delivery system. For example, a GSE may be reconstituted into liposomes for delivery to target cells. Liposomes are spherical lipid bilayers with aqueous interiors. All molecules that are present in an aqueous solution at the time of liposome formation (in this case, oligonucleotides) are incorporated into this aqueous interior. The liposomal contents are both protected from the external microenvironment and, because liposomes fuse with cell membranes, are efficiently delivered into the cell cytoplasm, obviating the need to neutralize the oligonucleotides' negative charge.

In cases where the GSEs are expressed as polypeptides, specific initiation signals may also be required for efficient translation of inserted GSE sequences. Exogenous translational control signals, including the ATG initiation codon, must be provided. Furthermore, the initiation codon must be in frame with the reading frame of the GSE sequence to ensure translation of the entire insert. These exogenous translational control signals and initiation codons can be of a variety of origins, both natural and synthetic.

The efficiency of expression of GSEs in cells into which they are introduced also may be modulated by the inclusion in the delivery vector of a variety of regulatory elements. These include, but are not limited to, appropriate transcription enhancer elements, transcription terminators, etc. (see Bittner et al., 1987, *Methods in Enzymol.* 153:516–544).

The isolated GSEs suppress HIV activity by either encoding polypeptide or RNA products. The present invention encompasses any such polypeptide product, including fusion proteins, leader peptides and localization signals. In addition, anti-sense RNA, DNA molecules and ribozymes that function to inhibit HIV infection are also within thee scope of the invention.

Methods for introducing GSE polynucleotides into cells or tissues include the insertion of naked polynucleotide, i.e., by injection into tissue, the introduction of a GSE in a cell ex vivo, i.e., for use in autologous cell therapy, the use of a vector such as a virus, retrovirus, phage or plasmid, etc. or techniques such as electroporation which may be used in vivo or ex vivo.

The GSEs may be formulated and administered through a variety of means, including systemic, localized, or topical administration. Techniques for formulation and administration may be found in "Remington's Pharmaceutical Sciences," Mack Publishing Co., Easton, Pa., latest edition. The mode of administration may be selected to maximize delivery to a desired target site in the body.

For systemic administration, routes of injection include intramuscular, intravenous, intraperitoneal, and subcutaneous. The polynucleotides of the invention are formulated in aqueous solutions, preferably in physiologically compatible buffers such as Hanks's solution, Ringer's solution, or physiological saline buffer. In addition, the polynucleotides may be formulated in solid or lyophilized form, then redissolved or suspended immediately prior to use.

Inhibitors of Cellular Genes and Gene Products Suppress HIV Infection

A number of GSEs selected from human cell-derived RFE libraries have been shown to have derived from specific portions of several known cellular genes. For example, several independently selected GSEs have substantial sequence identity (90–100%) with cDNAs of genes encoding certain subunits of NADH dehydrogenase. The lack of complete identity between the GSEs and the cellular gene sequences may have resulted from genetic polymorphism between different individuals or mutations introduced during cloning or PCR amplification. Section 7, infra, demonstrates that an inhibitor of NADH dehydrogenase gene expression inhibits HIV infection in primary human T cell cultures. Therefore, the present invention also encompasses inhibitors of cellular genes and gene products which have been identified as cellular targets during HIV infection.

Once a cellular gene has been identified as a potentially important target for supporting the HIV life cycle, assay systems may be established using such genes for the screening and selection of additional compounds as anti-HIV therapeutics based on their ability to down-regulate the expression of the gene or inhibit the activities of its gene product. For example, a cell line which naturally expresses the gene of interest or has been transfected with it may be incubated with various compounds. A reduction of the expression of the gene of interest or an inhibition of the activities of its encoded product may be used as a read-out. The compounds are retested in other assays such as in OM10.1 cells or in productive HIV infection to confirm their activities against HIV infection. These compounds may be screened from known organic compounds, products of peptide libraries and products of chemical combinatorial libraries.

In the case of NADH dehydrogenase, a large number of small molecule inhibitors are available in the art. Such inhibitors may be used in the methods of the present invention. An in vitro assay may be established to screen for additional NADH dehydrogenase complex I inhibitors by measuring membrane potential of live cells with DiOC6, a dye which accumulates in the mitochondrial and cytoplasmic membrane depending on mitochondrial functional activities and ATP concentrations (*Methods in Enzymology*, 1995, 260:448). Compounds are selected for their ability to decrease membrane potential by methods well known in the art.

The subsections below describe several cellular genes which have been identified herein as important targets for the development of HIV therapeutics. Inhibitors of these genes and their gene products may be used to inhibit HIV infection.

NADH Dehydrogenase

In aerobic organisms, adenosine triphosphate (ATP) provides the major source of energy. For the generation of ATP, energy rich molecules such as NADH and $FADH_2$ are first formed in glycolysis, fatty acid oxidation and the citric acid cycle. When these molecules donate their electrons to molecular oxygen, free energy is released to generate ATP.

Oxidative phosphorylation is the process by which ATP is formed as electrons are transferred from NADH or $FADH_2$ to $O_2$ by a series of electron carriers (Stryer, 1988, *Biochemistry*, Freeman). This process occurs in the mitochondria of eukaryotic cells. More specifically, the enzymes that catalyze the electron transport chain reside in the inner membrane of mitochondria, and they are encoded by both nuclear and mitochondrial DNA. These enzymes exist as large protein complexes, and the first complex of the chain is known as NADH dehydrogenase or NADH-Q reductase. It has a molecular weight of 850,000 daltons and consists of over 40 polypeptide subunits, seven of which are encoded by the mitochondrial genome. (Anderson et al., 1981, *Nature* 290:457; Chomyn et al., 1985, *Nature* 314:592; Chomyn et al., 1986, *Science* 234:619) The nucleotide sequences of the cDNAs of nuclear genes for the subunits have been described (Walker et al., 1992, *J. Mol. Biol.* 226:1051; Fearnley et al., 1989, *EMBO J.* 8:665; Pilkington et al., 1989, *Biochem* 28:3257) NADH dehydrogenase catalyzes the transfer of electrons from NADH to an electron carrier termed ubiquinone.

Since NADH dehydrogenase inhibitors suppress HIV infection, other therapeutically suitable agents that inhibit the expression and/or function of NADH dehydrogenase are also encompassed within the scope of the present invention. These inhibitors include small molecules as well as anti-sense and ribozyme molecules that interfere with NADH dehydrogenase subunit gene expression. Examples of other inhibitors include, but not limited to, Amytal, Annonin VI, Aurachin A, Aurachin B, Aureothin, Benzimidazole, Bullactin, Capsaicin, Ethoxyformic anhydride, Ethoxyquin, Fenpyroximate, Mofarotene (Ro 40-8757; arotinoids), Molvizarin, Myxalamide PI, Otivarin (annonaceous acetogenins), Pethidine, Phenalamid $A_2$, Phenoxan, Piericidin A, p-chloromercuribenzoate, Ranolazine (RS-43285), Rolliniasatin-1, Rolliniasatin-2, Rotenone, Squamocin, and Thiangazole (Singer and Ramsay, 1992, *Mol. Mechan. in Bioenergetics* Chap. 6, p.153; Degli Espasti et al., 1994, *Biochem. J.* 301:161; Friedrich et al., 1994, *Eur. J. Biochem.* 219:691; Uchida et al., 1994, *Int. J. Cancer* 58:891; Wyatt et al., 1995, *Biochem. Pharmacol.* 50:1599; Shimomura et al., 1989, *Arch. Biochem Biophy.* 270:573)

2-oxoglutarate Dehydrogenase

The 2-oxoglutarate dehydrogenase complex catalyzes oxidative decarboxylation of 2-oxoglutarate to succinyl-CoA and $CO_2$, and is the rate-limiting enzyme which controls the flux of substrates through the Krebs cycle (Delvin, T. M., ed, 1992, *Textbook of Biochemistry*, Wiley-Liss, Inc.). This enzyme complex is located in the inner membrane/matrix compartment of the mitochondria. The complex consists of multiple copies of 2-oxoglutarate dehydrogenase (lipoamide) [OGDH or ELO; 2-oxoglutarate: lipoamide 2-oxidoreductase (decarboxylating and acceptor succinylating), EC 1.2.4.2], dihydrolipoamide succinyltransferase (designated E20; EC 2.3.1.61) and dihydrolipoamide dehydrogenase (E3; EC 1.8.1.4). The coding sequence of 2-oxoglutarate dehydrogenase has been described (GenBank Accession Nos. D10523 and D90499; Koike et al., 1992, *Proc. Natl. Acad. Sci. U.S.A.* 89:1963–1967; Koike, 1995, *Gene* 159:261–266). A number of inhibitors for 2-oxoglutarate dehydrogenase have been described (Majamaa et al., 1985, *Biochem. J.* 229:127–133).

Pyruvate Kinase

Pyruvate kinase/thyroid hormone binding protein p58 (TBP) is a monomer of pyruvate kinase (ATP pyruvate $O_2$ phosphotransferase, EC 2.7.1.40) subtype M2. Its conversion to the tetrameric pyruvate kinase is regulated by fructose 1,6,-bisphosphate (Fru-1,6-$P_2$). At low glucose concentrations mammalian cells contain low Fru-1,6-$P_2$ and pyruvate kinase is inactive. At high glucose concentration (regular medium contains 5–10 mM glucose), high levels of Fru-1,6-$P_2$ are found in proliferating and tumor cells, which require high pyruvate kinase activity for growth. It has been demonstrated that low Fru-1,6-$P_2$ favors formation of p58 and high concentration convert it to the tetrameric enzyme. An increase in glucose concentration could lead to multimerization of p58 which in turn activates pyruvate kinase and glycolysis. At the same time thyroid hormone is released from the complex with TBP and might bind to nuclear and mitochondrial receptors and activate oxidative phosphorylation. The coding sequence of pyruvate kinase/thyroid hormone binding protein has been described (GenBank Accession No. M26252; Kato et al., 1989, *Proc. Natl. Acad. Sci. U.S.A.* 86:7861–7865).

Calnexin

Calnexin is a type I membrane protein which functions as a molecular chaperon for secretory glycoproteins in the endoplasmic reticulum (ER) with ATP and $Ca^{++}$ as two cofactors involved in the substrate binding (Ou et al., 1995, *J. Biol. Chem.* 270:18051). It has been demonstrated that folding of gp120 is mediated by calnexin during the translocation of the newly synthesized gp120 into ER (Li et al., 1996, *Proc. Natl. Acad. Sci. U.S.A.* 93:9606). The coding sequence of calnexin has been described (GenBank Accession No. L10284; David et al., 1993, *J. Biol. Chem.* 268:9585–9592).

ADP-ribosylation Factor 3

ADP-ribosylation factors (ARFs) are guanine nucleotide binding proteins of about 20kDa molecular weight that stimulate ADP-ribosyltransferase activity of cholera toxin in vitro (Tsai et al., 1991, *J. Biol. Chem.* 266:23053–23059). Five different ARFs have been cloned from human cDNA. ARF3 is represented by two mRNAs of 3.7 and 1.2 kb that are generated through the use of alternative polyadenylation signals (Tsai et al., 1991, supra).

Methods to Down-regulate Cellular Gene Expression

In addition to small molecule inhibitors, any methods known in the art which down-regulate the expression and/or function of the cellular genes described in Sections 5.7.1–5.7.5, supra are also encompassed by the invention. For example, anti-sense RNA and DNA molecules may be used to directly block the translation of mRNA encoded by these cellular genes by binding to targeted mRNA and preventing protein translation. Polydeoxyribonucleotides can form sequence-specific triple helices by hydrogen bonding to specific complementary sequences in duplexed DNA. Formation of specific triple helices may selectively inhibit the replication and/or gene expression of targeted genes by prohibiting the specific binding of functional trans-acting factors.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of cellular RNA sequences. Antisense RNA showing high affinity binding to target sequences can-also be used as ribozymes by addition of enzymatically active sequences known to those skilled in the art.

Polynucleotides to be used in triplex helix formation should be single stranded and composed of deoxynucleotides. The base composition of these polynucleotides must be designed to promote triple helix formation via Hoogsteen base pairing rules, which generally require sizeable stretches of either purines or pyrimidines to be present on one strand of a duplex. Polynucleotide sequences may be pyrimidine-based, which will result in TAT and CGC triplets across the three associated strands of the resulting triple helix. The pyrimidine-rich polynucleotides provide base complementarity to a purine-rich region of a single strand of the duplex in a parallel orientation to that strand. In addition, polynucleotides may be chosen that are purine-rich, for example, containing a stretch of G residues. These polynucleotides will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" polynucleotide. Switchback polynucleotides are synthesized in an alternating 5'-3', 3'-5' manner, such that they base pair with first one strand of a duplex and then the other, eliminating the necessity for a sizeable stretch of either purines or pyrimidines to be present on one strand of a duplex.

Both anti-sense RNA and DNA molecules, and ribozymes of the invention may be prepared by any method known in the art. These include techniques for chemically synthesizing polydeoxyribonucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into host cells.

Various modifications to the nucleic acid molecules may be introduced as a means of increasing intracellular stability and half-life. Possible modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Pharmaceutical Formulations and Routes of Administration of Inhibitors

Inhibitory compounds of the expression of genes encoding NADH dehydrogenase, 2-oxoglutarate dehydrogenase, pyruvate kinase, calnexin and ADP-ribosylation factor 3, as well as inhibitors of their encoded products, can be administered to a human patient in need of such treatment, by themselves, or in pharmaceutical compositions where an inhibitor is mixed with suitable carriers or excipient(s). A therapeutically effective dose refers to that amount of the compound sufficient to result in an inhibition of HIV infection as compared to the pre-treatment condition. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than systemic manner, for example, via injection of the compound directly into a specific tissue, often in a depot or sustained release formulation.

Furthermore, one may administer the compound in a targeted drug delivery system, for example, in a liposome and/or conjugated with a cell-specific antibody. The liposomes and cell-specific antibody will be targeted to and taken up selectively by HIV-infected cells.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compound of the invention may be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the-form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a cosolvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the EC50 (effective dose for 50% increase) as determined in cell culture, i.e., the concentration of the test compound which achieves a half-maximal inhibition of HIV replication as assayed by the infected cells to retain CD4 expression, to reduce viral p24 or gp120, and to prevent syncytia formation. Such information can be used to more accurately determine useful doses in humans.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch.1, p.1).

Dosage amount and interval may be adjusted individually to provide plasma levels of the active moiety which are sufficient to maintain the inhibitory effects. Usual patient dosages for systemic administration range from 100–2000 mg/day. Stated in terms of patient body surface areas, usual dosages range from 50–910 mg/m$^2$/day. Usual average plasma levels should be maintained within 0.1–1000 $\mu$M.

In cases of local administration or selective uptake, the effective local concentration of the compound may not be related to plasma concentration.

The amount of composition administered will, of course, be dependent on the subject being treated, on the subject's body surface area, the severity of the affliction, the manner of administration and the judgment of the prescribing physician.

Example

Isolation and Identification of Human Cell-derived GSEs Exhibiting HIV-suppressive Activities Materials and Methods Construction of RFE Libraries Two RFE libraries were constructed from cDNAs of two human cell lines according to the method described by Gudkov et al. (1994, Proc. Natl. Acad. Sci. USA 91:3744). The cDNA prepared from HL-60 cells and HeLa cells was partially digested with DNaseI in the presence of Mn$^{++}$ (Sambrook et al., 1989, Molecular Cloning A Laboratory Manual, Cold Spring Harbor Laboratory, N.Y.). Under these conditions, DNaseI is known to produce mostly double-stranded breaks.

The resulting fragments were repaired with the Klenow fragment of DNA polymerase I and T4 polymerase and ligated to synthetic double-stranded adaptors. The 5' adaptors (SEQ ID NOS: 11 and 12) were:

```
5'-CTCGGAATTCAAGCTTATGGATGGATGG
    3'CCTTAAGTTCGAATACCTACCTAC-5'
```

The 3' Adaptors (SEQ ID NOS: 13 and 14) were:

```
5'TGAGTGAGTGAATCGATGGATCCGTCT
 ACTCACTCACTTAGCTACCTAGGCAGATCCT-5'
```

In the case of the library made from HL-60 cells, mRNA from uninduced cells was first substracted from mRNA from cells induced with TNF-α. The subtracted HL-60 library represents a modification of the procedure described in Coche et al., 1994, *Nucleic Acids Res.* 22:1322–1323. The tracer mRNA was purified from HL-60 cells containing the LNCX plasmid at different time points after induction with TNF-α. The LNCX gene was used as an internal standard to monitor the enrichment of the sequences present in the tracer after subtraction. mRNA isolated from induced and uninduced cells was annealed separately to oligo dT magnetic beads (Dyna) and the first cDNA strand was synthesized using reverse transcriptase and oligo dT as the primer. The RNA strand was hydrolyzed and the second strand was synthesized on the induced population using a primer containing three ATG codons and 10 random nucleotides on the 3' end. Single stranded cDNA fragments were annealed to an excess of driver cDNA attached to the magnetic beads. This procedure was repeated several times until substantial enrichment in the spiked LNCX sequence was seen. The final population of single-stranded DNA (ssDNA) molecules was amplified using primers with three TGA codons in all three reading frames with 10 random nucleotides on the 3' end. The resulting population of cDNA fragments were cloned into LNCX. This step was taken to enrich for mRNA encoded by cellular genes that might be important in supporting certain stages of the HIV life cycle in order to compensate for the low efficiency of retroviral transfer into OM10.1 cells. This library was represented by 10$^6$ recombinant clones.

The random fragments of cDNA from HeLa cells were subjected to a normalization procedure to provide for uniform abundance of different DNA sequences (Gudkov and Roninson, 1997, *Methods in Molecular Biology* 69:221, Humana Press, Inc., Totowa, N.J.). This procedure was used to increase the probability of isolating GSEs from rare cDNAs, since total polyA$^+$ RNA was a mixture of unequally represented sequences. In brief, the method first denatured 20 $\mu$g of cDNA by boiling for 5 min. in 25 $\mu$l of TE buffer, followed by immediate cooling on ice. Then, 25 $\mu$l of 2×hybridization solution was added, and the mixture was divided into four aliquots in Eppendorf tubes, 12.5 $\mu$l each. One to two drops of mineral oil were added to each sample to avoid evaporation, and the tubes were placed into a 68° C. water bath for annealing. One tube was frozen every 12 hours. After the last time-point, each of the annealing mixtures was diluted with water to a final volume of 500 $\mu$l and subjected to hydroxylapatite (HAP) chromatography. HAP suspension equilibrated with 0.01 M phosphate-buffered saline (PBS) was placed into Eppendorf tubes so that the volume of HAP pellet was approximately 100 $\mu$l. The tubes with HAP and all the solutions used below were preheated and kept at 65° C. The excess of PBS was removed, and diluted annealing solution was added. After mixing by shaking in a 65° C. water bath, the tubes were left in the water bath until HAP pellet was formed (a 15-s centrifugation was used to collect the pellet without exceeding 1000 g in the microcentrifuge to avoid damage of HAP crystals). The supernatant was carefully replaced with 1 ml of preheated 0.01 M PBS, and the process was repeated. To elute the ssDNA, the HAP pellet was suspended in 500 $\mu$l of PBS at the single-strand elution concentration determined, e.g., 0.16M, the supernatant was collected, and the process was repeated. The supernatants were combined and traces of HAP were removed by centrifugation. ssDNA was concentrated by centrifugation, and washed three times using 1 ml of water on Centricon-100. The isolated ssDNA sequences were amplified by PCR with the sense primer from the adapter, using a minimal number of cycles to obtain 10 μg of the product. The size of the PCR product remained within the desired range (200–500 bp) was ascertained. The normalization quality was tested by Southern or slot-blot hybridization with $^{32}$P-labeled probes for high, moderate- and low-expressing genes using 0.3–1.0 μg of normalized cDNA/lane. β-actin and β-tubulin cDNAs were used as probes for high-expressing genes, c-myc and topo II cDNAs for moderate, and c-fos cDNA for low-expressing genes. cDNA isolated after different annealing times were compared with the original unnormalized cDNA. The probes were ensured to have a similar size and specific activity. The best-normalized ssDNA fraction was used, which produced the most uniform signal intensity with different probes, for large-scale PCR amplification to synthesize at least 20 μg of the product for cloning. More ssDNA template was used to obtain the desired amount by scaling up the number of PCR reactions or the reaction volume.

After normalization, the mixture of fragments ligated to adaptors was digested with BamHI and EcoRI, column purified and ligated to the retroviral vector pLNCX (Miller and Rosman, 1989, *BioTechniques* 7:980–990) or pLNG-FRM cut with EcoRI and BamHI. The pLNGFRM vector is the same as the pLNCX vector except that the neo$^r$ gene has been replaced with a truncated low affinity NGFR gene. The transduced cells express the truncated receptor on their surface which can be easily selected by an anti-NGFR antibody and FACS. The ligation mixture was transformed into *E. coli*. The total plasmid was purified from ~100,000 recombinant clones. The size distribution of the cloned fragments was tested by PCR amplification using primers derived from the vector sequences adjacent to the adapters.

Cell Lines and Reagents

The OM10.1 cells are available from the American Type Culture Collection, Manassas, Va. as CRL 10850 (Butera, U.S. Patent No. 5,256,534). The CEM-ss cells are available from the NIH AIDS Research and Reference Reagent Program as Cat. No. 776. HIV-1$_{SF2}$ is available from NIH AIDS Research and Reference Reagent Program as Cat. No. 275. HL-60 cells are available from American Tissue Culture Collection as CCL 240. HIV-1$_{IIIB}$ is available from AIDS Program as Cat. No. 398.

The anti-CD4 (Q4120PE) and anti-p24 (KC-57 FITC) antibodies were purchased from Sigma and Coulter, respectively. TNF-α was obtained from Boehringer Mannheim. G418 was purchased from Gibco/BRL as Geneticin. The anti-NGFR antibody was obtained from ATCC (HB-8737) as hybridoma 20.4 (U.S. Pat. Nos. 4,786,593 and 4,855,241). Two anti-CD4 antibodies (L77 and L120) were obtained from Becton Dickenson.

Transduction and Selection of GSE

The libraries prepared from HL-60 cells according to the method of Section 6.1.1. supra, were transfected into the packaging cell line, PA317 (ATCC CRL #9078), and converted into retrovirus for infection of OM10.1 cells. Libraries in pLNCX vector were co-cultured and selected with G418. Libraries in pLNGFRM vector were transduced by spinoculation (centrifugation of target cells at 1200×g for 90 min. in the presence of filtered retroviral supernatant) and selected by FACS sorting of the NGFR$^+$ population. After selection, the OM10.1 cells harboring the entire RFE library were induced with 10 U/ml of TNF-α at 37° C., and 24 hours later, were stained with an antibody and sorted for CD4 expression. Genomic DNA from the CD4$^+$ cells was purified and used for PCR amplification of inserts with the vector-derived primers. The amplified mixture was digested with EcoRI and BamHI and cloned back into the retroviral vector. The selection was repeated for additional rounds.

Additionally, a normalized RFE library made from HeLa cells was transferred into CEM-ss cells and the neo resistant population was infected with TCID$_{50}$ of 3000/10$^6$ cells of HIV-1$_{IIIB}$. This RFE library was represented by 50×10$^6$ independent recombinant clones. Four and seven days after infection, a purified anti-CD4 monoclonal antibody, L77 (Becton Dickinson), was added at 5 μg/ml to prevent syncytia formation. Syncytia formation is thought to be prevented by blocking the interaction between gp120 expressed on the surface of an infected cell and CD4 on the surface of an uninfected cell. Antibody L77 does not prevent HIV infection of a cell. At 10–12 days after infection, CD4$^+$, p24$^-$ cell populations representing uninfected cells were sorted. Genomic DNA from the CD4$^+$, p24$^-$ cells was purified and used for PCR amplification of inserts with the vector-derived primers. The amplified mixture was digested with EcoRI and BamHI and cloned back into the retroviral vector. The selection was repeated for additional rounds.

Immunoflurorescence and Flow Cytometry

For the immunofluorescent staining of CD4$^+$ cells for selection, 10$^7$ cells were washed twice with Assay Buffer (500 ml PBS, 1 ml of 0.5 mM of EDTA at pH 8, 0.5 ml of 10% sodium azide and 10 ml of fetal bovine serum), and resuspended in 500 μl PBS to which 50 μl of anti-CD4 antibody (Q4120 PE, Sigma) was added. After incubation at 4° C. for 30 min., 5 ml of Assay Buffer was added and the cells centrifuged at 1200 rpm for 4 min. The cells were washed twice with Assay Buffer before sorting by FACS. The aforementioned procedure was performed under sterile conditions.

In order to determine p24 expression in HIV-infected cells, the cells were first washed twice with Assay Buffer. About 10$^6$ cells were suspended in 100 μl Assay Buffer, mixed with 2 ml of Ortho PermeaFix Solution (Ortho Diagnostics), and incubated for 40 min. at room temperature. After centrifugation at 1200 rpm for 4 min. at 4° C., the cells were resuspended in 2 ml Wash Buffer (500 ml PBS, 25 ml fetal bovine serum, 1.5% bovine serum albumin and 0.0055% EDTA) for 10 min. at room temperature. After centrifugation, the cells were resuspended in 50 μl Wash Buffer and mixed with 1:500 dilution of an IgG$_{2a}$ antibody for 20 min. at 4° C., followed by incubation with 5–10 μl of anti-p24 antibody (KC57-FITC, Coulter) for 30 min. at 4° C. The cells were then washed twice with Wash Buffer and analyzed by flow cytometry.

For the selection of NGFR$^+$ cells, 10$^7$ cells were washed twice with Assay buffer and resuspended in 200 μl Assay buffer plus 5% normal mouse serum, and 2 ml of anti-NGFR-PE antibody was added. After incubation at 4° C. for 30 min., 5 ml of Assay buffer was added and the cells were centrifuged at 1200 rpm for 4 min. The cells were washed twice with Assay buffer before sorting by FACS.

Recovery of GSEs and Sequence Analysis

Genomic DNA was isolated from the selected population of OM10.1 or CEM-ss cells harboring putative GSEs by resuspending the cell pellet in 0.1% Triton X-100, 20μg/ml proteinase K in 1×PCR buffer, incubating at 55° C. for 1 hour, and boiling for 10 minutes. Genomic DNA was used for PCR amplification using vector-derived primers, cloned into the retroviral vector, and transformed into *E. coli* using techniques well known in the art. Individual plasmids were purified from *E. coli* clones using QIAGEN plasmid kits. Inserts were sequenced by the dideoxy procedure (AutoRead Sequencing Kit, Pharmacia Biotech) and run on a Pharmacia LKB A.L.F. DNA sequencer. Sequences were analyzed using the DNASTAR program.

Results

Two selection strategies were used to isolate human cell-derived GSEs with HIV-suppressive activities from RFE libraries. One strategy selected for GSEs which suppressed productive infection of cells by HIV. The second strategy selected for GSEs which suppressed induction of the latent provirus in OM10.1 cells. When OM10.1 cells were treated with TNF-α and stained with an antibody specific for the cell surface molecule CD4, a rapid loss of CD4 expression was observed (FIG. 1). In contrast, the vast majority of the uninduced OM10.1 cells retained CD4 expression. It is believed that activation of the latent virus in OM10.1 cells by TNF-α leads to the production of viral protein gp120, which binds to cytoplasmic CD4, thereby preventing its translocation to the cell surface. A diminution of CD4$^+$ OM10.1 cells also correlates with an increased production of viral protein p24 in the cells following TNF-α induction.

GSEs derived from cDNAs representing expressed human cellular genes were identified and isolated from a RFE library made from HL-60 cells using HIV provirus activation in OM10.1 cells as a read-out. Following transfection of the entire library into a packaging cell line, retrovirus carrying the library was used to infect OM10.1 cells by co-cultivation or spinoculation, and NGFR selection was performed to ensure the retention of the viral vector. When the infected cells were treated with TNF-α, a small number of residual CD4$^+$ cells were detected by an anti-CD4 antibody and sorted by FACS. The GSEs contained in these cells were recovered by PCR amplification and their nucleotide sequences determined.

Figure 3:
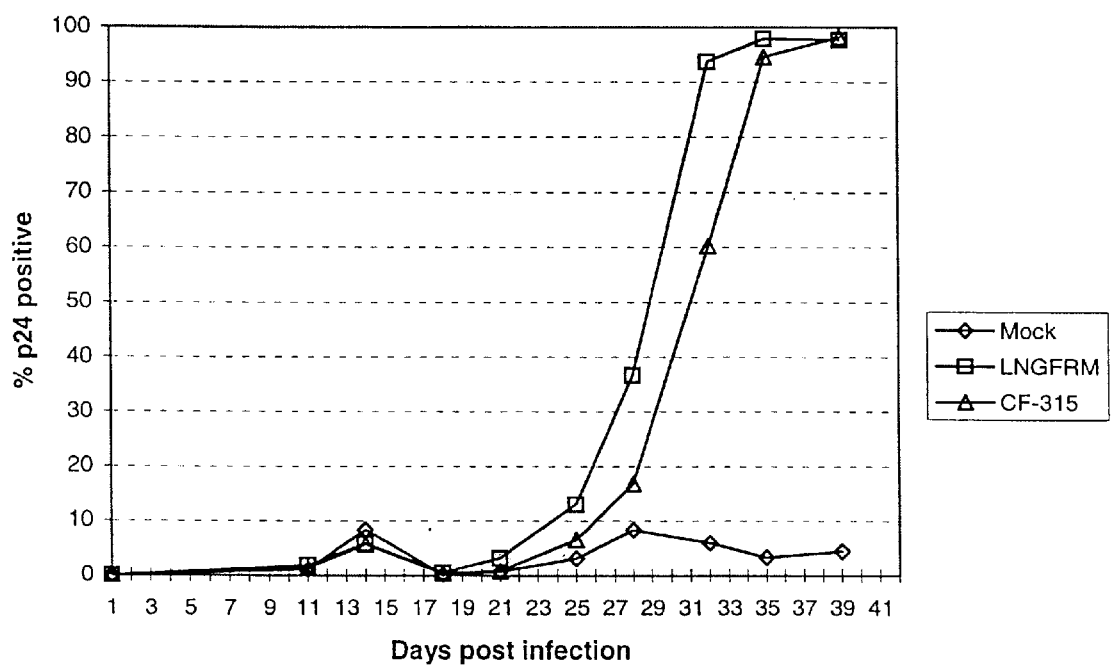
FIG. 3. Percentage of intracellular p24+ CEM-ss cells containing the CF-315 sequence (SEQ ID NO:1) after infection with HIV-1$_{SF2}$ at a TCID$_{50}$ of 1000. CEM-ss cells ($10^6$) containing the C-315 construct or control vector DNA denoted as LNGFRM were harvested on the indicated days post infection, stained with FITC-conjugated anti-p24 and analyzed by flow cytometry. Mock infected, ◊; LNGFRM vector-infected, □; and C-315 infected, Δ.

A total of ten GSEs were isolated by the two aforementioned selection strategies. Six of these GSEs were shown to have substantial sequence identity with cDNAs of genes encoding different subunits of the NADH dehydrogenase enzyme complex. For example, CF-315 (SEQ ID NO:1) is a GSE which suppresses HIV replication as an antisense molecule, which in its sense orientation has sequence identity with a gene encoding a subunit, ND6, of a mitochondrial enzyme, NADH dehydrogenase (Chomyn et al., 1988, *Science* 234:614) (FIG. 2). CF-315 was further shown to protect uninfected human T cells from a productive HIV-1 infection (FIG. 3). In this experiment, the retroviral vector, pLNGFRM, containing the CF-315 polynucleotide was transferred into CEM-ss cells followed by NGFR selection. Vector containing plasmid DNA (denoted LNGFRM) was used as negative control. The NGFR$^+$ cells were 99% CD4$^+$, and they were then infected with TCID$_{50}$ of 1000 of HIV-1$_{SF2}$. The infected cells were removed at 11, 14, 18, 21, 25, 28, 32, 35 and 39 days after infection, and stained with a fluorescinated-anti-p24 antibody as an indicator of HIV infection. FIG. 3 shows that CF-315 inhibited infection of human T cells by HIV-1$_{SF2}$, as compared with negative control of vector plasmid DNA.

CF-319 (SEQ ID NO:2) is a GSE which suppresses HIV replication in the sense orientation and has substantial sequence identity with another portion of the gene encoding the ND6 subunit of NADH dehydrogenase (FIG. 4). CF-101 (SEQ ID NO:3) also exhibits its HIV-suppressive activities in the sense orientation and has substantial sequence identity with a gene encoding the ND2 subunit of NADH dehydrogenase (FIG. 5) (Chomyn et al., 1985, *Nature* 314:592). CF-117 (SEQ ID NO:4) suppresses HIV activities as an antisense molecule, and in its sense orientation, it has substantial sequence identity with a gene encoding the ND6 subunit of NADH dehydrogenase (FIG. 6). CF-025 (SEQ ID NO:5) suppresses HIV infection as an antisense molecule, and in its sense orientation, it has substantial sequence identity with a gene encoding the ND2 subunit of NADH dehydrogenase (FIG. 7). CF-128 (SEQ ID NO:6) suppresses HIV infection in the sense orientation and it has substantial sequence identity with a gene encoding the ND4 subunit of NADH dehydrogenase (FIG. 8).

Since both selection strategies produced GSEs having substantial sequence identity with different subunits of NADH dehydrogenase, this enzyme complex may play an important role during HIV infection, and thus, methods to down-regulate the expression of this complex or any of its subunits may be used to inhibit HIV replication in infected cells.

The selection of GSEs from HeLa cell library using productive infection of CEM-ss cells isolated four additional polynucleotides which have substantial sequence identity with other cellular genes. CF-004 (SEQ ID NO:7) suppresses HIV infection as a sense molecule and has substantial sequence identity with a gene encoding human 2-oxoglutarate dehydrogenase (FIG. 9) (Koike, 1995, *Gene* 158:261–266; Koike et al., 1992, *Proc. Natl. Acad. Sci. U.S.A.* 89:1963–1967). CF-113 (SEQ ID NO:8) suppresses HIV infection as a sense molecule and has substantial sequence identity with a gene encoding human M2-type pyruvate kinase and cytosolic thyroid hormone binding protein (FIG. 10) (Kato et al., 1989, *Proc. Natl. Acad. Sci. U.S.A.* 86:7861–786S). CF-204 (SEQ ID NO:9) suppresses HIV infection as an antisense molecule, and in its sense orientation, it has substantial sequence identity with a gene encoding human calnexin (FIG. 11) (David et al., 1993, *J. Biol. Chem.* 268:9585–9592). CF-001 (SEQ ID NO:10) suppresses HIV infection as an antisense molecule, and in its sense orientation, it has substantial sequence identity with a gene encoding human ADP-ribosylation factor 3 (FIG. 12) (Tsai et al., 1991, *J. Biol. Chem.* 266:23053–23059).

Figure 13:
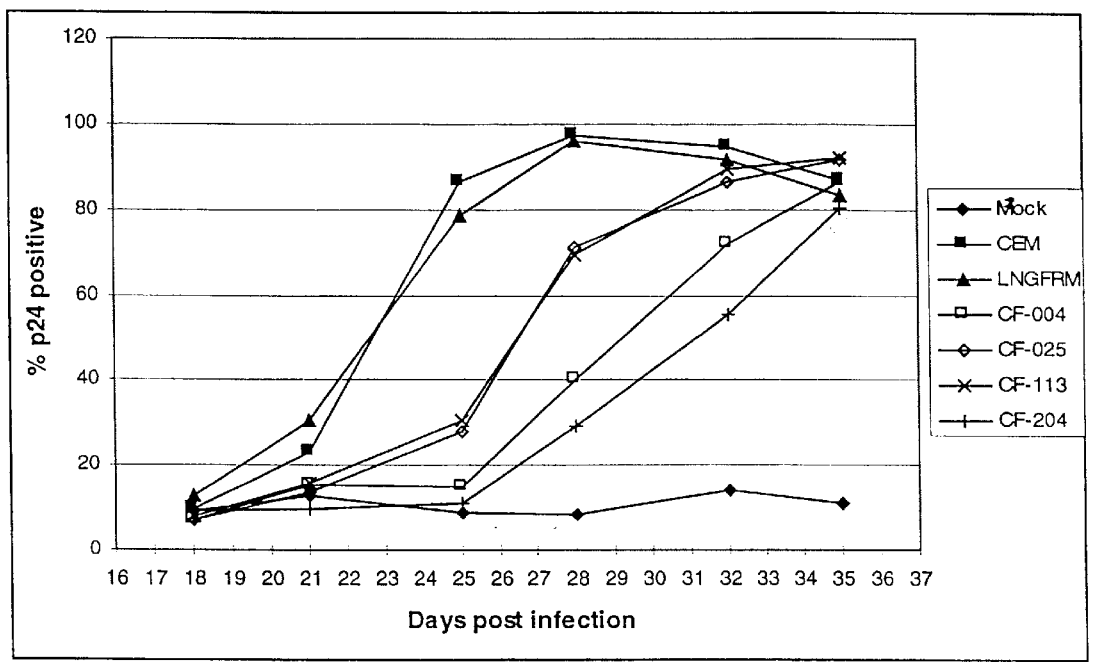
FIG. 13. Percentage of intracellular p24+ CEM-ss cells containing various GSEs: CF-004 (SEQ ID NO:7), CF-025 (SEQ ID NO:5), CF-113 (SEQ ID NO:8) and CF-204 (SEQ ID NO:9) after infection with HIV-1$_{SF2}$ at a TCID$_{50}$ of 1000. Controls include mock-infected, vector (LNGFRM)-infected and HIV-infected CEM-ss cells.
Figure 14:
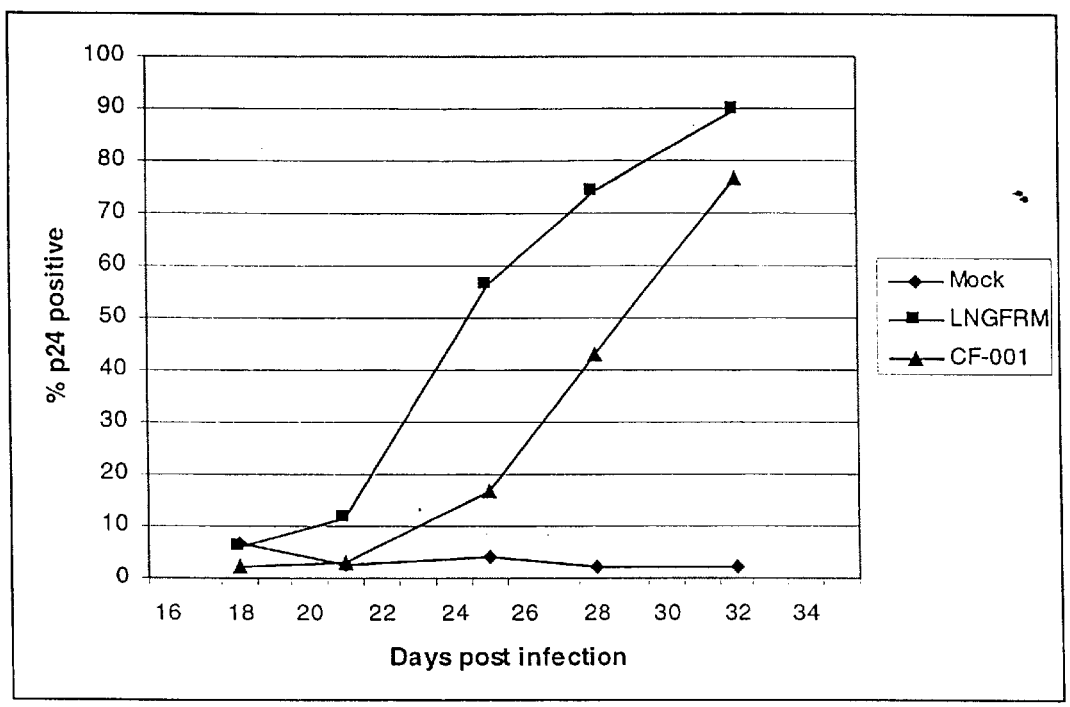
FIG. 14. Percentage of intracellular p24+ CEM-ss cells containing CF-001 (SEQ ID NO:10) after infection with HIV-1$_{SF2}$ at a TCID$_{50}$ of 1000. Controls include mock-infected and vector (LNGFRM)-infected cells.

FIG. 13 shows the HIV-suppressive activities of four of the aforementioned GSEs in preventing productive infection of CEM-ss cells by HIV. While the GSEs were isolated as fragments of distinct cellular genes, they all inhibited HIV infection as shown by a reduction of p24 levels in the infected cells when compared with controls. Additionally, FIG. 14 shows the HIV-suppressive activities of CF-001 which functions as an antisense molecule.

Example

NADH Dehydrogenase Inhibitors Suppress HIV Infection

Material and Methods

NADH Dehydrogenase Inhibitors

NADH dehydrogenase inhibitors, amytal (Sigma) and mofarotene (Uchida et al., 1994 *Int. J. Cancer* 58:891–897), were diluted in sterile culture medium and used according to the indicated concentrations Inhibition Assays OM10.1 cells were cultured in RPMI 1640 glucose-free media prior to and during incubation with NADH dehydrogenase inhibitors and TNF-α induction. The inhibitors were added to the cells followed by TNF-α induction 1–2 hours later. The expression of CD4 by the cells was assessed by anti-CD4 antibody staining and flow cytometry after 24 hour incubation at 37° C.

Infection of Freshly Isolated CD4+ Cells

Human peripheral blood leukocytes (PBLs) were isolated using Ficoll-Hypaque density gradient separation. Cells were washed twice and resuspended in RPMI+10% FBS+2% human AB serum+penicillin/streptomycin/glutamine+100 Units/ml of IL-2 at a concentration of $0.5 \times 10^6$ cells/ml. PBLs were then activated with phytohemagglutinin at 0.5 μg/ml and placed in a humidified incubator at 37° C./5% $CO_2$. After two days of activation, $10^6$ cells were infected with HIV-$1_{SF33}$ at $TCID_{50}$ of 1000, in the presence of various concentrations of mofarotene: 0 μM, 1 μM, 0.5 μM, 0.1 μM, and 0.05 μM. A separate set of uninfected samples under identical concentrations of mofarotene were also maintained as controls. The samples were analyzed by flow cytometry at day 4 and day 6 post infection. The cells were gated for CD3 expression (for T cells). Then the expression of CD4 and viral p24 and CD4 was examined by bivariate dot plot.

Results

Figure 15:
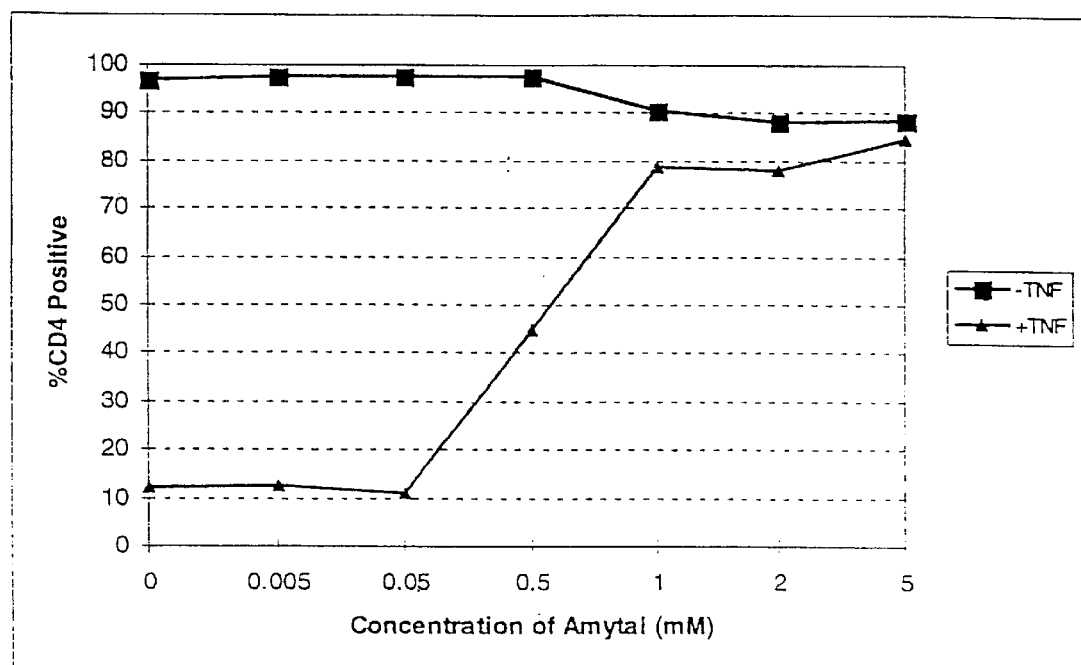
FIG. 15. Percentage of CD4+ OM10.1 cells after treatment with amytal following TNF-α induction. TNF induction, ▲; no TNF induction, ■.
Figure 16:
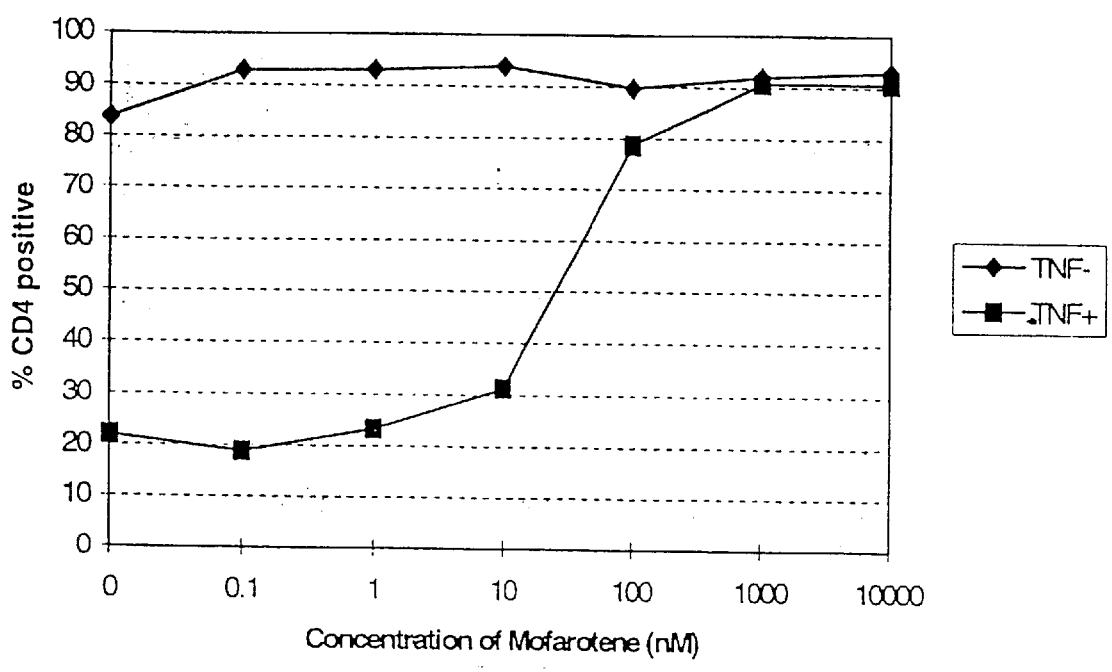
FIG. 16. Percentage of CD4+ OM10.1 cells after treatment with mofarotene following TNF-α induction. TNF induction, ■; no TNF induction, ♦.

Since several GSEs have been selected and shown to have substantial sequence identity with cellular genes which encode different subunits of NADH dehydrogenase, two compounds with known NADH dehydrogenase-inhibitory activities were tested for their ability to suppress HIV infection. FIG. 15 shows that amytal inhibited the induction of latent HIV provirus in OM10.1 cells in a dose-dependent manner, as shown by its ability to retain CD4 expression by TNF-α-induced OM10.1 cells. In the same assay, mofarotene, which down-regulates mitochondrial gene expression, also inhibited HIV-1 induction at even lower concentrations (FIG. 16). At 100 nM of mofarotene, 80% of the cells retained CD4 expression, and greater than 80% of the cells remained viable. In addition, when p24 expression was measured as an indication by HIV infection, both amytal and mofarotene also suppressed intracellular p24 levels in the treated cells as compared with untreated controls.

In order to test the ability of a NADH dehydrogenase inhibitor to prevent productive infection of T cells by HIV, human PBLs were isolated and infected with $HIV_{SF33}$ in the presence of various concentrations of mofarotene. The CD3+ T cells were analyzed with respect to their expression of CD4 and viral p24 and the results are shown in Table 1.

TABLE 1

| HIV | Mofarotene (μM) | % CD4+ in T cell population | % p24+ in CD4+ T population |
|---|---|---|---|
| − | 1.0 | 36% | 0% |
| − | 0.5 | 34% | 0% |
| − | 0.1 | 34% | 0% |
| − | 0.05 | 33% | 0% |
| − | 0.0 | 32% | 0% |
| + | 1.0 | 25% | 10% |
| + | 0.5 | 24% | 12.5% |
| + | 0.1 | 28% | 11.4% |
| + | 0.05 | 18% | 20.5% |
| + | 0.0 | 15% | 33% |

On day 4 post-infection, there was little detectable difference between PBLs infected with HIV whether or not mofarotene was added. Mofarotene alone did not significantly alter the percentage of CD4+ T cells, nor did it alter the expression level of CD3 on the cell surface.

On day 6, a significant difference was detected with respect to the percentage of CD4+ T cells and percentage of p24+ CD4+ T cells. In the HIV-infected sample without mofarotene, 33% of CD4+ T cells were p24+ and only 15% of T cells were CD4+. In the HIV-uninfected control sample, ~32% of T cells were CD4+, suggesting a dramatic depletion of CD4+ T cells by HIV infection. In the HIV-infected sample with 1 μM of mofarotene, only 10% of CD4+ T cells were p24+. In addition, ~25% of T cells were CD4+, indicating that mofarotene inhibited the depletion of CD4+ T cells by HIV infection. The level of protection by mofarotene, as measured by the percentage of p24+ CD4+ T cells and percentage of CD4+ cells in the CD3+ T cell population, diminished with decreased concentrations of mofarotene. While mofarotene alone increased the percentage of CD4+ T cells in uninfected samples, the effect was minimal (up to 4% higher). At day 6, mofarotene did not alter the expression level of CD3 on the cell surface. Hence, a NADH dehydrogenase inhibitor prevented productive infection by HIV of primary cultures of human T cells.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for selecting HIV inhibitors, comprising the steps of:
   a) exposing NADH dehydrogenase-expressing cells to a test compound;
   b) measuring expression or enzymatic activity of NADH dehydrogenase in the cells; and
   c) selecting a compound that down-regulates NADH dehydrogenase expression or NADH dehydrogenase enzymatic activity,
   wherein said selected test compound inhibits HIV infection.

2. A method according to claim 1 wherein expression of NADH dehydrogenase is measured using an antibody.

3. A method according to claim 1 wherein expression of NADH dehydrogenase is measured by hybridization to a nucleic acid probe with cellular RNA.

4. A method for selecting HIV inhibitors, comprising the steps of:
   a) exposing 2-oxoglutarate dehydrogenase-expressing cells to a test compound;
   b) measuring expression or enzymatic activity of 2-oxoglutarate dehydrogenase in the cells; and
   c) selecting a compound that down-regulates 2-oxoglutarate dehydrogenase expression or 2-oxoglutarate dehydrogenase enzymatic activity,
   wherein said selected test compound inhibits HIV infection.

5. A method according to claim 4 wherein expression of 2-oxoglutarate dehydrogenase is measured using an antibody.

6. A method according to claim 4 wherein expression of 2-oxoglutarate dehydrogenase is measured by hybridization to a nucleic acid probe with cellular RNA.

7. A method for selecting HIV inhibitors, comprising the steps of:
   a) exposing pyruvate kinase-expressing cells to a test compound;
   b) measuring expression or enzymatic activity of pyruvate kinase in the cells; and
   c) selecting a compound that down-regulates pyruvate kinase expression or pyruvate kinase enzymatic activity,
   wherein said selected test compound inhibits HIV infection.

8. A method according to claim 7 wherein expression of pyruvate kinase is measured using an antibody.

9. A method according to claim 7 wherein expression of pyruvate kinase is measured by hybridization to a nucleic acid probe with cellular RNA.

10. A method for selecting HIV inhibitors, comprising the steps of:
    a) exposing calnexin-expressing cells to a test compound;
    b) measuring expression or enzymatic activity of calnexin in the cells; and
    c) selecting a compound that down-regulates calnexin expression or calnexin enzymatic activity,
    wherein said selected test compound inhibits HIV infection.

11. A method according to claim 10 wherein expression of calnexin is measured using an antibody.

12. A method according to claim 10 wherein expression of calnexin is measured by hybridization to a nucleic acid probe with cellular RNA.

13. A method for selecting HIV inhibitors, comprising the steps of:
    a) exposing ADP ribosylation factor 3 inhibitor-expressing cells to a test compound;
    b) measuring expression or enzymatic activity of ADP ribosylation factor 3 inhibitor in the cells; and
    c) selecting a compound that down-regulates ADP ribosylation factor 3 inhibitor expression or ADP ribosylation factor 3 inhibitor enzymatic activity,
    wherein said selected test compound inhibits HIV infection.

14. A method according to claim 13 wherein expression of ADP ribosylation factor 3 inhibitor is measured using an antibody.

15. A method according to claim 13 wherein expression of ADP ribosylation factor 3 inhibitor is measured by hybridization to a nucleic acid probe with cellular RNA.

* * * * *

SEQUENCE LISTING

<160> NUMBER OF SEQ ID NOS: 14

<210> SEQ ID NO 1
<211> LENGTH: 135
<212> TYPE: DNA
<213> ORGANISM: Homo sapiens

<400> SEQUENCE: 1
agatcctatt ggtgcgtggg ctttgtatga ttatgggcgt agattagtag tagttactgg     60

```
ttgaacattg tttgttggtg tatatattgt aattgggatt gctcggggga ataggttatg    120
tgattaggag taggg                                                    135

<210> SEQ ID NO 2
<211> LENGTH: 100
<212> TYPE: DNA
<213> ORGANISM: Homo sapiens

<400> SEQUENCE: 2
gatcctcccg aatcaaccct gacccctctc cttcataaat tattcagctt cctacactat    60
taaagtttac cacaaccacc acgccatcat actccttcac                         100

<210> SEQ ID NO 3
<211> LENGTH: 143
<212> TYPE: DNA
<213> ORGANISM: Homo sapiens

<400> SEQUENCE: 3
catcagccct tcttaacatc tacttctacc tacgcctaat ctactccacc tcaatcacac    60
tactccccat atctaacaac gtaaaaataa aatgacagtt tgagcataca aacccaccc    120 cattcctccc cacactcatc gcc                                          143

<210> SEQ ID NO 4
<211> LENGTH: 100
<212> TYPE: DNA
<213> ORGANISM: Homo sapiens

<400> SEQUENCE: 4
gtgaaagagt atgatggggt ggtggttgtc gtaaacttta atagtgtagg aagctgaata    60
atttataaag gagaggggac agggttgatt cgggaggatc                        100

<210> SEQ ID NO 5
<211> LENGTH: 116
<212> TYPE: DNA
<213> ORGANISM: Homo sapiens

<400> SEQUENCE: 5
gaagaagcag gccggatgtc agaggggtgc cttgggtaac ctctgggact cagaagtgaa    60 aggggggctat tcctagtttt attgctatag ccattatgat tattaatgat gagtat      116

<210> SEQ ID NO 6
<211> LENGTH: 127
<212> TYPE: DNA
<213> ORGANISM: Homo sapiens

<400> SEQUENCE: 6
tcctagtcct cacaatcatg gcaagccagc gccacttatc cagtgaacca ctatcacgaa    60
aaaaactcta cctctctata ctaatctccc tacaaatctc attaattata atattcacaa   120
ccacaga                                                            127

<210> SEQ ID NO 7
<211> LENGTH: 105
<212> TYPE: DNA
<213> ORGANISM: Homo sapiens

<400> SEQUENCE: 7
gcgcaaagca cgcgacatgg tggggcaggt ggccatcaca aggattgagc agctgtcgcc    60
attccccttt gacctcctgc tgaaggaggt gcagaagtac cccaa                  105
```

<210> SEQ ID NO 8
<211> LENGTH: 105
<212> TYPE: DNA
<213> ORGANISM: Homo sapiens

<400> SEQUENCE: 8
gaaatcctgg aggccagtga tgggatcatg gtggctcgcg gtgatctagg cattgagatt      60
cctgcagaga aggtcttcct tgctcagaag atgataattg gacgg                      105

<210> SEQ ID NO 9
<211> LENGTH: 107
<212> TYPE: DNA
<213> ORGANISM: Homo sapiens

<400> SEQUENCE: 9
ggttgtcaat cacaggtcgc caggagacac cacatccagg agctgactca catctagggt      60
tggcaatctg aggagcctcc cattctccat ccatgtcttc atcccaa                    107

<210> SEQ ID NO 10
<211> LENGTH: 121
<212> TYPE: DNA
<213> ORGANISM: Homo sapiens

<400> SEQUENCE: 10
ccacattgaa cccaatggta gggatggtgg tgacgatctc ccccagtttc agcttgtata      60
ggatggtggt ctttcctgcg gcatccaggc ccaccatcag gatgcgcatc tccttcttcc      120
c                                                                      121

<210> SEQ ID NO 11
<211> LENGTH: 28
<212> TYPE: DNA
<213> ORGANISM: Homo sapiens

<400> SEQUENCE: 11
ctcggaattc aagcttatgg atggatgg                                         28

<210> SEQ ID NO 12
<211> LENGTH: 23
<212> TYPE: DNA
<213> ORGANISM: Homo sapiens

<400> SEQUENCE: 12
ccttaagttc gaatactacc tac                                              23

<210> SEQ ID NO 13
<211> LENGTH: 27
<212> TYPE: DNA
<213> ORGANISM: Homo sapiens

<400> SEQUENCE: 13
tgagtgagtg aatcgatgga tccgtct                                          27

<210> SEQ ID NO 14
<211> LENGTH: 30
<212> TYPE: DNA
<213> ORGANISM: Homo sapiens

<400> SEQUENCE: 14
actcactcac ttagctacca ggcagatcct                                       30